United States Patent
Kenmoku et al.

(10) Patent No.: US 6,911,521 B2
(45) Date of Patent: Jun. 28, 2005

(54) POLYHYDROXYALKANOATE THAT COMPRISES UNIT HAVING SUBSTITUTED OR UNSUBSTITUTED (PHENYLMETHYL) SULFANYL STRUCTURE IN SIDE CHAIN THEREOF AND PROCESS FOR PRODUCING THE SAME

(75) Inventors: Takashi Kenmoku, Kanagawa (JP); Etsuko Sugawa, Kanagawa (JP); Tetsuya Yano, Kanagawa (JP); Tsuyoshi Nomoto, Tokyo (JP); Takeshi Imamura, Kanagawa (JP); Tomohiro Suzuki, Kanagawa (JP); Tsutomu Honma, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 422 days.

(21) Appl. No.: 10/157,142

(22) Filed: May 30, 2002

(65) Prior Publication Data

US 2003/0096384 A1 May 22, 2003

(30) Foreign Application Priority Data

| May 31, 2001 | (JP) | 2001/165239 |
| May 31, 2001 | (JP) | 2001/165357 |
| Jul. 10, 2001 | (JP) | 2001/209898 |
| Jul. 10, 2001 | (JP) | 2001/210039 |
| Feb. 15, 2002 | (JP) | 2002/039259 |

(51) Int. Cl.[7] .................. C08G 63/02; C08G 63/78; C12P 11/00
(52) U.S. Cl. .................. 528/295; 435/135; 435/252.34; 528/272; 528/274; 528/293; 528/353; 528/354; 528/360; 560/9; 560/15; 560/51; 560/53
(58) Field of Search .................. 435/130, 252.34, 435/135; 528/272, 274, 353, 354, 60, 293, 295; 560/9, 15, 51, 53

(56) References Cited

U.S. PATENT DOCUMENTS

| 4,393,167 A | 7/1983 | Holmes et al. ............... 525/64 |
| 4,477,654 A | 10/1984 | Holmes et al. ............. 528/361 |

(Continued)

FOREIGN PATENT DOCUMENTS

| EP | 1 113 033 A2 | 7/2001 |
| EP | 1 130 042 A2 | 9/2001 |
| EP | 1 130 043 A2 | 9/2001 |
| EP | 1 188 782 A2 | 3/2002 |
| EP | 1 236 752 A2 | 9/2002 |
| EP | 1 236 754 A2 | 9/2002 |
| EP | 1 236 755 A2 | 9/2002 |
| EP | 1 245 605 A2 | 10/2002 |
| EP | 1 253 161 A2 | 10/2002 |
| EP | 1 253 162 A2 | 10/2002 |
| EP | 1 263 161 A2 | 10/2002 |
| EP | 1 262 508 A2 | 12/2002 |
| EP | 1 275 727 A2 | 1/2003 |
| JP | 59-190945 | 10/1984 |
| JP | 63-226291 | 9/1988 |
| JP | 5-7492 | 1/1993 |
| JP | 5-93049 | 4/1993 |
| JP | 6-15604 | 3/1994 |
| JP | 7-14352 | 2/1995 |
| JP | 7-265065 | 10/1995 |
| JP | 8-19227 | 2/1996 |
| JP | 2642937 | 5/1997 |
| JP | 9-191893 | 7/1997 |
| JP | 2001-178484 | 7/2001 |
| JP | 2001-288256 | 10/2001 |
| WO | WO 97/07153 A1 | 2/1997 |
| WO | WO 02/16627 A2 | 2/2002 |

OTHER PUBLICATIONS

Katharina Fritzsche et al., "An Unusual Bacterial Polyester with a Phenyl Pendant Group," 191 *Makromol. Chem.* 1957–1965 (1990).

(Continued)

*Primary Examiner*—Herbert J. Lilling
(74) *Attorney, Agent, or Firm*—Fitzpatrick, Cella, Harper & Scinto

(57) ABSTRACT

A polyhydroxyalkanoate that comprises a unit represented by the following chemical formula (1):

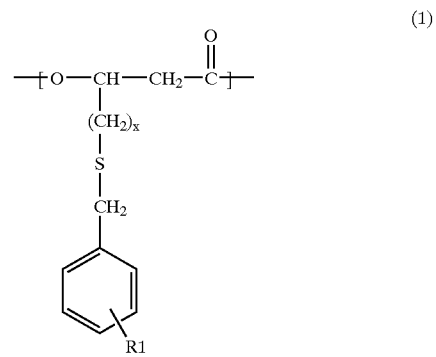

$x = 1-8$ wherein R1 is a substituent of an aromatic ring selected from the group consisting of H, $CH_3$, $C_2H_5$, $CH_3CH_2CH_2$, $(CH_3)_2CH$, $(CH_3)_3C$, a halogen atom, CN, $NO_2$, COOR', and $SO_2R''$, wherein R' is selected from the group consisting of H, Na, K, $CH_3$, and $C_2H_5$, and R" is selected from the group consisting of OH, a halogen atom, ONa, OK, $OCH_3$, and $OC_2H_5$; and x represents an integer of 1 to 8 being the same or different each other in the polyhydroxyalkanoate. A method for producing the polyhydroxyalkanoate is also provided.

37 Claims, 6 Drawing Sheets

U.S. PATENT DOCUMENTS

| | | | |
|---|---|---|---|
| 4,876,331 A | 10/1989 | Doi et al. | 528/361 |
| 5,135,859 A | 8/1992 | Witholt et al. | 435/135 |
| 5,191,016 A | 3/1993 | Yalpani | 525/54.2 |
| 5,200,332 A | 4/1993 | Yamane et al. | 435/135 |
| 5,292,860 A | 3/1994 | Shiotani et al. | 528/361 |
| 5,334,698 A | 8/1994 | Witholt et al. | 528/354 |
| 5,811,272 A | 9/1998 | Snell et al. | 435/135 |
| 6,156,852 A | 12/2000 | Asrar et al. | 525/450 |
| 6,492,147 B2 | 12/2002 | Imamura et al. | 435/135 |
| 6,521,429 B2 | 2/2003 | Honma et al. | 435/135 |
| 6,635,782 B2 | 10/2003 | Honma et al. | 560/53 |
| 6,645,743 B1 | 11/2003 | Honma et al. | 435/146 |
| 6,649,380 B1 | 11/2003 | Yano et al. | 435/135 |
| 2001/0029039 A1 | 10/2001 | Honma et al. | 435/135 |
| 2001/0031488 A1 | 10/2001 | Imamura et al. | 435/135 |
| 2002/0052444 A1 | 5/2002 | Imamura et al. | 525/107 |
| 2003/0013841 A1 | 1/2003 | Imamura et al. | 528/271 |
| 2003/0096182 A1 | 5/2003 | Yano et al. | 430/108.5 |
| 2003/0104300 A1 | 6/2003 | Kenmoku et al. | 430/108.22 |
| 2003/0113368 A1 | 6/2003 | Nomoto et al. | 424/450 |
| 2003/0194789 A1 | 10/2003 | Honma et al. | 435/135 |
| 2003/0207412 A1 | 11/2003 | Kenmoku et al. | 435/135 |

OTHER PUBLICATIONS

Y.B. Kim et al., "Preparation and Characterization of Poly(β–hydroxyalkanoates) Obtained from *Pseudomonas oleovorans* Grown with Mixtures of 5–Phenylvaleric Acid and *n*–Alkanoic Acids," 24 *Macromol*. 5256–5260 (1991).

Safwat Antoun et al., "Production of Chiral Polyester by *Pseudomonas oleovorans* Grown with 5–Phenyl–2,4–Pentadienoic Acid," 3 *Chirality* 492–494 (1991).

Helmut Ritter et al., "Bacterial Production of Polyesters Bearing Phenoxy Groups in the Side Chains, 1 Poly(3–hydroxy–5–phenoxypentanoate–*co*–3–hydroxy–9–phenoxy–nonanoate) from *Pseudomonas oleovorans*," 195 *Macromol. Chem. Phys*. 1665–1672 (1994).

Yasuo Takagi et al., "Biosynthesis of Polyhydroxyalkanoate with a Thiophenoxy Side Groups Obtained from *Pseudomonas putida*," 32 *Macromol*. 8315–8318 (1999).

YoungBaek Kim et al., "Poly–3–hydroxyalkanoates Produced from *Pseudomonas oleovorans* Grown with ω–Polyhydroxyalkanoates," 29 *Macromol*. 3432–3435 (1996).

Ohyoung Kim et al., "Bioengineering of Poly(β–hydroxyalkanoates) for Advanced Material Applications: Incorporation of Cyano and Nitrophenoxy Side Chain Substituents," 41 (Supp. 1) *Can. J. Microbiol*. 32–43 (1995).

Peter I. Djurovich et al., "Ir(III) Cyclometalated Complexes as Efficient Phosphorescent Emitters in Polymer Blend and Organic LEDs," 41(1) *Polymer Reprints* 770–771 (2000).

Joanne M. Curley et al., "Production of Poly(3–hydroxyalkanoates) Containing Aromatic Substituents by *Pseudomonas oleovorans*," 29 *Macromol*. 1762–1766 (1996).

C.D. Lytle et al., "Filtration Sizes of Human Immunodeficiency Virus Type 1 and Surrogat Viruses Used to Test Barrier Materials," 58(2) *Appl. & Environm. Microbiol*. 747–749 (1992).

Richard Ashby et al., "A Tunable Switch to Regulate the Synthesis of Low and High Molecular Weight Microbial Polyesters," 62(1) *Biotechnol. Bioeng*. 106–113 (1999).

Leigh A. Madden et al., "Chain Termination in Polyhydroxyalkanoate Synthesis: Involvement of Exogenous Hydroxy–Compounds as Chain Transfer Agents," 25 *Intl. J. Biol. Macromol*. 43–53 (1999).

Gerhart Braunegg et al., "Polyhydroxyalkanoates, Biopolyesters from Renewable Resources: Physiological and Engineering Aspects," 65 *J. Biotechnol*. 127–161 (1998).

A. Steinbüchel et al., "Molecular Basis for Biosynthesis and Accumulation of Polyhydroxyalkanoic Acids in Bacteria," 103 *FEMS Microbiol. Rev*. 217–230 (1992).

Fengying Shi et al., "Use of Poly(ethylene glycol)s to Regulate Poly(3–hydroxybutyrate) Molecular Weight During *Alcaligenes eutrophus* Cultivations," 29 *Macromol*. 7753–7758 (1996).

Herbert Ulmer et al., "Bacterial Production of Poly(β–hydroxyalkanoates) Containing Unsaturated Repeating Units by *Rhodospirillum rubrum*," 27 *Macromol*. 1675–1679 (1994).

Marianela Andújar et al., "Polyesters Produced by *Pseudomonal oleovorans* Containing Cyclohexyl Groups," 30 *Macromol*. 1611–1616 (1997).

J.K. Stille et al., "Tetracyclic Dienes. I. The Diels–Alder Adduct of Norbornadiene and Cyclopentadiene," 81 *J. Am. Chem. Soc*. 4273–4275 (Aug. 1959).

G.J.M. de Koning et al., "A Biodegradable Rubber by Crosslinking Poly(Hydroxyalkanoate) From *Pseudomonas oleovorans*," 35(10) *Polymer* 2090–2097 (1994).

Moon Yeun Lee et al., "Crosslinking of Microbal Copolyesters with Pendant Epoxide Groups by Diamine," 40 *Polymer* 3787–3793 (1999).

M.Y. Lee et al., "Hydrophilic Bacterial Polyesters Modified with Pendant Hydroxyl Groups," 41 *Polymer* 1703–1709 (2000).

Suzette M. Aróstegui et al., "Bacterial Polyesters Produced by *Pseudomonas oleovorans* Containing Nitrophenyl Groups," 32 *Macromol*. 2889–2895 (1999).

Richard A. Gross et al., "Cyanophenoxy–Containing Microbal Polyesters: Structural Analysis, Thermal Properties, Second Harmonic Generation and In–Vivo Biodegradability," 39 *Polymer International* 205–213 (1996).

Marianela Andújar et al., "Polyesters produced by *Pseudomonal oleovorans* Containing Cyclohexyl Groups," 30 *Macromol*. 1611–1615 (1997).

Won Ho Park et al., "Epoxidation of Bacterial Polyesters with Unsaturated Side Chains. I. Production and Epoxidation of Polyesters From 10–Undecanoic Acid," 31 *Macromol*. 1480–1486 (1998).

Won Ho Park et al., "Epoxidation of Bacterial Polyesters with Unsaturated Side Chains. II. Rate of Epoxidation and Polymer Properties," 36 *J. Polym. Sci*. 2381–2387 (1998).

Young B. Kim t al., "Poly(β–hydroxyalkanoate) Copolymers Containing Brominated Repeating Units Produced by *Pseudomonas oleovorans*," 25 *Macromol*. 1852–1857 (1992).

Roland G. Lageveen et al., "Formation of Polyesters by *Pseudomonas oleovorans*: Effect of Substrates on Formation and Composition of Poly–(R)–3–Hydroxyalkanoates and Poly–(R)–3–Hydroxyalkenoates," 54(12) *Appl. Environ. Microbiol*. 2924–2932 (1988).

Yoshiharu Doi et al., "Biosynthesis and Characterization of a New Bacterial Copolyest r of 3–Hydroxyalkanoates and 3–Hydroxy–ω–Chloroalkanoates," 23 *Macromol*. 3705–3707 (1990).

Kuno Jung et al., "Characterization of New Bacterial Copolyesters Containing 3–Hydroxyalkanoates and Acetoxy–3–Hydroxyalkanoates," 33 *Macromol.* 8571–8575 (2000).

Alan Grund et al., "Regulation of Alkane Oxidation in *Pseudomonas putida*," 123(2) *J. Bacteriol.* 546–556 (1975).

Katsutoshi Hori et al., "Production of Poly(3–Hydroxyalkanoates–co–3–Hydroxy–ω–Fluoroalkanoates) by *Pseudomonal oleovorans* from 1–Fluorononane and Gluconate," 16(5) *Biotechnol. Lett.* 501–506 (May 1994).

Marieta Constantin et al., "Chemical Modification of Poly-(hydroxyalkanoates). Copolymers Bearing Pendant Sugars," 20 *Macromol. Rapid Commun.* 91–94 (1999).

Alexander Steinbüchel et al., "Diversity of Bacterial Polyhydroxyalcanoic Acids," 128 *FEMS Microbiol. Lett.* 219–228 (1995).

European Search Report in Application No. 02012096.0 (Jan. 10, 2003).

POLYHYDROXYALKANOATE THAT COMPRISES UNIT HAVING SUBSTITUTED OR UNSUBSTITUTED (PHENYLMETHYL) SULFANYL STRUCTURE IN SIDE CHAIN THEREOF AND PROCESS FOR PRODUCING THE SAME

BACKGROUND OF THE INVENTION

1. Field of the Invention

The present invention relates to a polyhydroxyalkanoate (hereinafter, also referred to as "PHA" for short) that comprises a novel structural unit and a process for producing the same. More particularly, the present invention relates to a novel biodegradable PHA that comprises 3-hydroxyalkanoic acid units having a substituted or unsubstituted (phenylmethyl)sulfanyl group at the end of the side chain thereof, and to a process for producing PHAs from an alkanoic acid having a substituted or unsubstituted (phenylmethyl)sulfanyl group at the end of the side chain thereof by using a microorganism capable of producing PHA and accumulating it in the cell.

2. Related Background Art

It has been reported that various microorganisms can produce poly-3-hydroxybutyrate (hereinafter, also referred to as "PHB" for short) or other PHA and accumulate it in the cell ("Biodegradable Plastics Handbook", Biodegradable Plastics Society Ed., NTS, pages 178–197 (1995)). These polymers may be utilized for production of various products by, for example, melt processing as with conventional plastics, but unlike many conventional synthetic polymer compounds, these polymers do not cause pollution in the natural environment because they are biodegradable, i.e., they are completely degraded by microorganisms in the natural world. Furthermore, they have good biocompatibility and their applications in the medical field as soft materials are expected.

Microbial PHAs are known to have different compositions and/or structures depending on, for example, the type of the microorganism, compositions of the culture medium, and culture conditions. Thus, studies have been done to control the composition and structure to improve physical properties of PHA.

(1) First, the following articles report or disclose synthesis of PHA by polymerization of relatively simple monomer units such as 3-hydroxybutyric acid (hereinafter, abbreviated as 3HB).

For instance, *Alcaligenes eutrophus* H16 (ATCC No. 17699) and mutants thereof are known to produce copolymers of 3-hydroxybutyrate and 3-hydroxyvalerate (hereinafter, abbreviated as 3HV) with various composition ratios (Japanese Patent Publication No. 6-15604 and Japanese Patent Publication Nos. 7-14352 and 8-19227.)

Japanese Patent No. 2642937 discloses production of PHA of $C_6$ to $C_{12}$ 3-hydroxyalkanoate monomer units by feeding acyclic aliphatic hydrocarbon compounds as substrates to *Pseudomonas oleovorans* (ATCC No. 29347).

Japanese Patent Application Laid-Open No. 5-7492 discloses a process for producing a copolymer of 3HB and 3HV using a microorganism such as *Methylobacterium* sp., *Paracoccus* sp., *Alcaligenes* sp., and *Pseudomonas* sp. in contact with $C_3$ to $C_7$ primary alcohol.

Japanese Patent Application Laid-Open No. 5-93049 and Japanese Patent Application Laid-Open No. 7-265065 disclose production of two-component copolymers of 3HB and 3-hydroxyhexanate by cultivating *Aeromonas caviae* with oleic acid or olive oil as a substrate.

Japanese Patent Application Laid-Open No. 9-191893 discloses that *Comamonans acidovorans* IFO 13852 produces polyester containing 3HB and 4-hydroxybutyrate as the monomer units when it is cultivated in the presence of gluconic acid and 1,4-butanediol as substrates.

The above-mentioned PHAs are "usual PHAs" including monomer units having an alkyl group as the side chain thereof, synthesized by microorganisms via β-oxidation of hydrocarbons etc. or via fatty acid synthesis from saccharides.

(2) However, "unusual PHAs", i.e., PHAs having a substituent other than an alkyl group on the side chain, are expected to be very useful when more extensive application of microbial PHAs is considered, for example, as functional polymers. Certain microorganisms have already been known to produce such "unusual PHAs", and it has been tried to improve physical properties of microbial PHA with such an approach.

Examples of the substituents include unsaturated hydrocarbons, ester groups, cyano groups, halogenated hydrocarbons, epoxides, and those containing an aromatic ring or rings. Of these, PHAs having an aromatic ring have been studied actively.

For example, Makromol. Chem., 191, 1957–1965 (1990), Macromolecules, 24, 5256–5260 (1991), and Chirality, 3, 492–494 (1991) report that *Pseudomonas oleovorans* produces PHAs containing 3-hydroxy-5-phenylvalerate (hereinafter, abbreviated as 3HPV) as the monomer unit, where changes in physical properties of the PHA are observed probably due to the presence of 3HPV.

Of the PHAs having a substituent on the side chain thereof, lately those having a phenoxy group on the side chain have been actively developed.

It has been reported that *Pseudomonas oleovorans* produces from 11-phenoxyundecanoic acids PHA made with monomer units of 3-hydroxy-5-phenoxyvalerate and 3-hydroxy-9-phenoxynonanoate (Macromol. Chem. Phys., 195, 1665–1672 (1994)).

Macromolecules, 29, 3432–3435 (1996) reports production of PHA having monomer units of 3-hydroxy-4-phenoxybutyrate and 3-hydroxy-6-phenoxyhexanoate from 6-phenoxyhexanoic acids; production of PHA having units of 3-hydroxy-4-phenoxybutyrate, 3-hydroxy-6-phenoxyhexanoate, 3-hydroxy-4-phenoxybutyrate, 3-hydroxy-6-phenoxyhexanoate and 3-hydroxy-8-phenoxyoctanoate from 8-phenoxyoctanoic acid; and production of PHA made with units of 3-hydroxy-5-phenoxyvaleric acid and 3-hydroxy-7-phenoxyheptanoic acid from 11-hydroxyundecanoic acid, by using *Pseudomonas oleovorans*.

Can. J. Microbiol., 41, 32–43 (1995) reports production of PHAs containing 3-hydroxy-6-(4-cyanophenoxy)hexanoic acids or 3-hydroxy-6-(4-nitrophenoxy)hexanoic acid as the monomer units by *Pseudomonas oleovorans* ATCC 29347 or *Pseudomonas putida* KT 2422 using octanoic acid and 6-(4-cyanophenoxy)hexanoic acid or 6-(p-nitrophenoxy) hexanoic acid as a substrate.

Of unusual PHAs developed, production of those having sulfur atoms in the form of sulfide (—S—) in the side chain thereof is reported in Macromolecules, 32, 8315–8318 (1999), where *Pseudomonas putida* 27N01 produced PHAs containing 3-hydroxy-5-(phenylsulfanyl)valeric acid and 3-hydroxy-7-(phenylsulfanyl)heptanoic acid as the monomer units, using octanoic acid and 11-(phenylsulfanyl) undecanoic acid as the substrates. In that case, the *Pseudomonas putida* 27N01 is pre-cultured in a culture medium containing octanoic acid only as the growth substrate, and then transferred to a culture medium that contains only 11-(phenylsulfanyl)undecanoic acid as a substrate.

Also Polymer Preprints, Japan Vol. 49, No. 5, 1034 (2000) reports production of PHAs containing two monomer units of 3-hydroxy-[(phenylmethyl)sulfanyl]valeric acid and 3-hydroxy-7-[(phenylmethyl)sulfanyl]heptanoic acid, by using *Pseudomonas putida* 27N01 and 11-[(phenylmethyl) sulfanyl]undecanoic acid as a substrate. In this case also, *Pseudomonas putida* 27N01 is precultured in a culture medium that contains only octanoic acid as the growth substrate, and then transferred to a culture medium that contains only 11-[(phenylmethyl)sulfanyl]undecanoic acid.

Concerning PHAs containing a 3-hydroxy-ω-[(phenylmethyl)sulfanyl]alkanoic acid unit among unusual PHAs, the above articles are the only reports on the biosynthesis of such PHAs. Further, the available production process is limited. Accordingly, the resulting polymers are not sufficient in types, purity, and yield. In the above process for producing the PHAs containing a 3-hydroxy-ω-[(phenylmethyl)sulfanyl]alkanoic acid unit, the polymer production is conducted by culturing the microorganism in a culture medium containing only ω-[(phenylmethyl)sulfanyl]alkanoic acid having a long carbon chain as the substrate, where ω-[(phenylmethyl)sulfanyl]alkanoic acid is also used as the growth substrate. Therefore, it is difficult to control the structure of the polymer.

PHAs containing a substituted 3-hydroxy-ω-[{[(substituted phenyl)methyl]sulfanyl}alkanoic acid unit that has a substituent such as various functional groups on the benzene ring of (phenylmethyl)sulfanyl group at the end of the side chain are PHAs having novel functionalities, and improvement in physical properties of such PHAs is predicted. Application of such PHAs will be expanded to novel fields where conventional PHAs have not been applicable. Thus, development of an efficient process for producing such PHAs is desired.

SUMMARY OF THE INVENTION

Through the intensive research to solve the above-mentioned problems by the present inventors, this invention was accomplished.

An object of the present invention is to provide a novel PHA and a process for producing the same, in which the PHA comprises a novel unit having a (phenylmethyl) sulfanyl structure in a substituted or unsubstituted side chain thereof.

According to one aspect of the present invention, there is provided a polyhydroxyalkanoate comprising a unit represented by the following chemical formula (1):

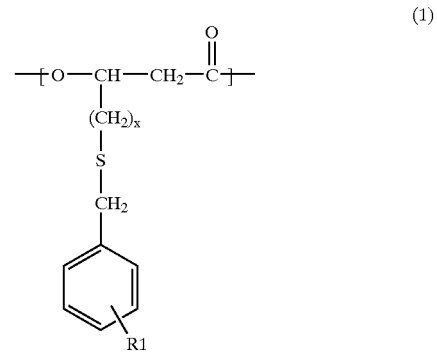

$x = 1-8$ wherein R1 is a substituent of an aromatic ring selected from the group consisting of H, $CH_3$, $C_2H_5$, $CH_3CH_2CH_2$, $(CH_3)_2CH$, $(CH_3)_3C$, a halogen atom, CN, $NO_2$, COOR', and $SO_2R''$, wherein R' is selected from the group consisting of H, Na, K, $CH_3$, and $C_2H_5$, and R'' is selected from the group consisting of OH, a halogen atom, ONa, OK, $OCH_3$, and $OC_2H_5$; and x represents an integer of 1 to 8 being the same or different each other in the polyhydroxyalkanoate, with the proviso that the polyhydroxyalkanoate does not consist of two units represented by the following chemical formulae (2) and (3):

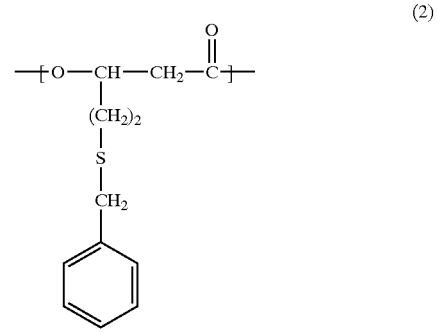

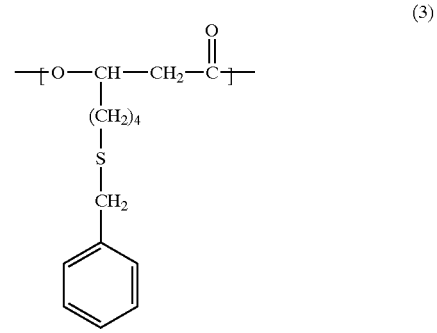

According to another aspect of the present invention, there is provided a process for producing a polyhydroxyalkanoate that comprises a unit represented by the chemical formula (1) comprising the step of cultivating a microorganism in a culture medium containing a compound represented by the following chemical formula (10):

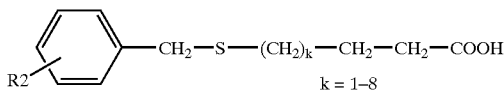

(10)

k = 1–8 wherein R2 is a substituent of an aromatic ring and selected the group consisting of H, $CH_3$, $C_2H_5$, $CH_3CH_2CH_2$, $(CH_3)_2CH$, $(CH_3)_3C$, a halogen atom, CN, $NO_2$, COOR' and $SO_2R''$, wherein R' is selected from the group consisting of H, Na, K, $CH_3$, and $C_2H_5$, and R'' is selected from the group consisting of OH, a halogen atom, ONa, OK, $OCH_3$, and $OC_2H_5$; and k represents an integer of 1 to 8.

DETAILED DESCRIPTION OF THE PREFERRED EMBODIMENT

Figure 1:
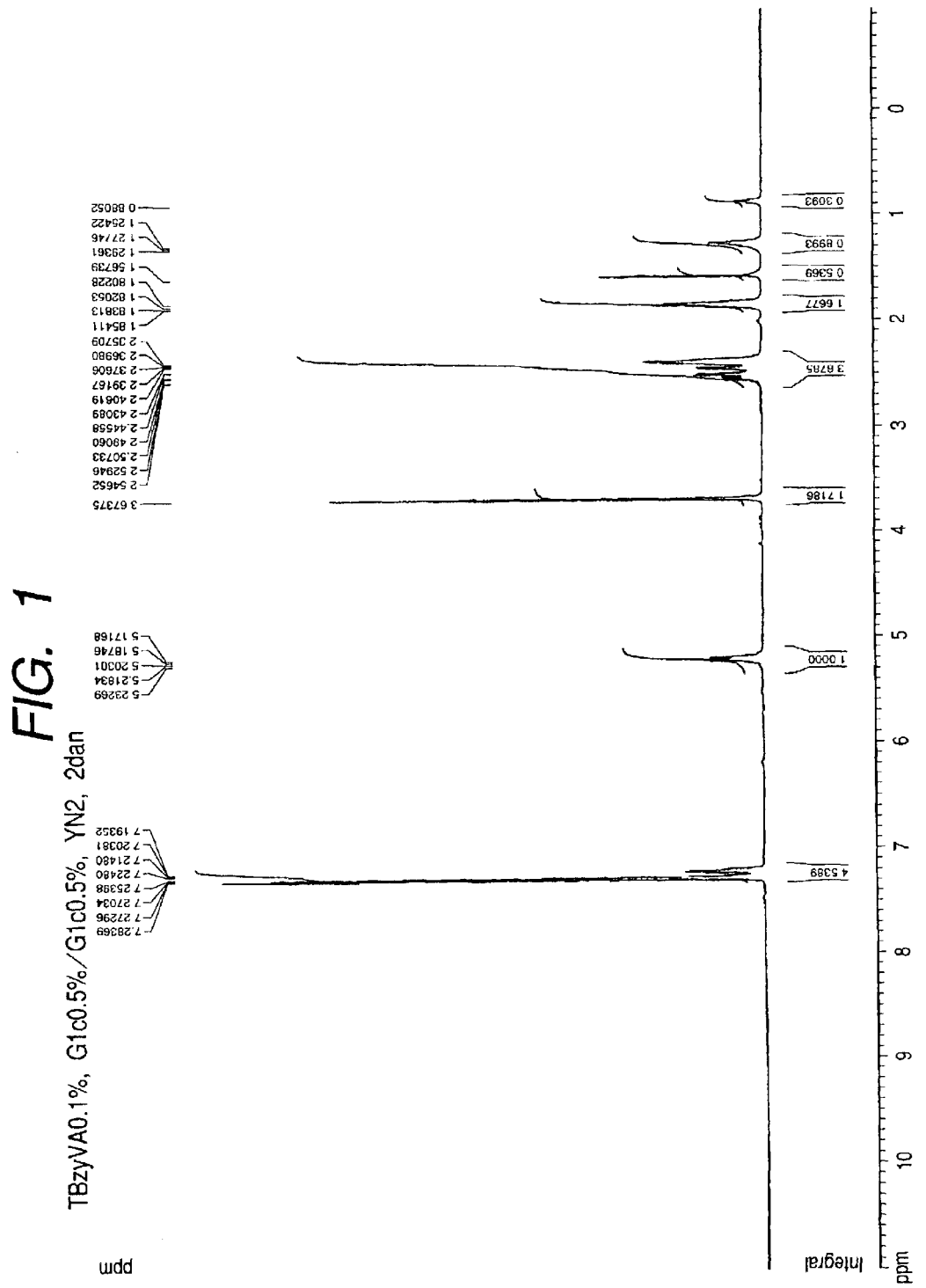
FIG. 1 shows the $^1H$ NMR spectrum of a polyhydroxyalkanoate obtained in Example 1.

A novel polyhydroxyalkanoate according to the present invention has a substituted or unsubstituted (phenylmethyl)sulfanyl structure on the side chain of a unit hydroxyalkanoic acid. This structure provides physical and chemical properties that are significantly different from those of known microbial polyhydroxyalkanoates.

The novel polyhydroxyalkanoate according to the present invention can be produced by the steps of: culturing a PHA producing microorganism in a culture medium containing a growth substrate and a substituted or unsubstituted ω-[(phenylmethyl)sulfanyl]alkanoic acid as a feedstock; and recovering polyhydroxyalkanoate containing units having a substituted or unsubstituted (phenylmethyl)sulfanyl group at the end of the side chain thereof, the polyhydroxyalkanoates being produced by accumulated in the microorganism during the cultivation step. In the microbial PHAs, the carbons at the 3 position of all 3-hydroxyalkanoic acid units including those represented by the chemical formula (1) are asymmetric carbons whose absolute configuration is R, indicating the biodegradability thereof.

Examples of the halogen atom in the substituent R on the benzene ring in the above general formulae (1) and (10) include fluorine, chlorine, and bromine.

The present invention is described more in detail below.

PHA-Producing Microorganisms

In the process for producing PHAs according to the present invention, any microorganisms can be used to produce PHA containing a unit having a substituted or unsubstituted (phenylmethyl)sulfanyl group at the end of the side chain thereof represented by the chemical formula (1) (hereinafter referred to as the subject PHA) so long as it can produce the subject PHA and accumulate it in the cells when cultivated in a culture medium containing a corresponding ω-[(phenylmethyl)sulfanyl]alkanoic acid represented by the chemical formula (10) as the source compound. For example, the microorganisms may be those belonging to the genus Pseudomonas having PHA-producing capabilities.

Examples of suitable microorganisms of genus Pseudomonas include the following three strains: Pseudomonas cichorii YN2 (FERM BP-7375), Pseudomonas cichorii H45 (FERM BP-7374), and Pseudomonas jessenii P161 (FERM BP-7376). These three microorganisms was first deposited as the national deposit by the applicant, and is deposited as the international deposit under the Budapest Treaty under the above-mentioned accession numbers in International Patent Organism Depositary, National Institute of Advanced Industrial Science and Technology, Independent Administrative Institution, Ministry of Economy, Trade and Industry 1–3, Higashi 1-chome, Tsukuba-shi, Ibaraki-ken, 305 JAPAN (former National Institute of Bioscience and Human-Technology (NIBH) of the Agency of Industrial Science and Technology, Ministry of Economy, Trade and Industry). They are also described in Japanese Patent Application No. 11-371863 (Japanese Patent Application Laid-Open No. 2001-178484) as novel strains capable of producing PHAs.

Bacteriological properties of the strains YN2, H45, and P161 are given below.

Bacteriological Properties of Strain YN2

(1) Morphological Properties

Shape and size of cells: rod, 0.8 μm×1.5 to 2.0 μm

Polymorphism of cells: negative

Mobility: motile

Sporulation: negative

Gram staining: negative

Colony shape: circular; entire, smooth margin; low convex; smooth surface; glossy; translucent (2) Physiological Properties Catalase: positive Oxidase: positive O/F test: oxidative (non-fermentative)

Nitrate reduction: negative

Indole production: positive

Acid production from glucose: negative

Arginine dihydrolase: negative

Urease: negative

Esculin hydrolysis: negative

Gelatin hydrolysis: negative

β-Galactosidase: negative

Fluorescent pigment production on King's B agar: positive

Growth under 4% NaCl: positive (weak growth)

Poly-β-hydroxybutyrate accumulation: negative (*)

Tween 80 hydrolysis: positive (*) Colonies cultured on nutrient agar were stained with Sudan Black for determination.

(3) Substrate Assimilation

Glucose: positive

L-Arabinose: positive

D-Mannose: negative

D-Mannitol: negative

N-Acetyl-D-glucosamine: negative

Maltose: negative

Potassium gluconate: positive n-Caprate: positive

Adipate: negative dl-Malate: positive

Sodium citrate: positive
Phenyl acetate: positive
Bacteriological Properties of Strain H45
(1) Morphological Properties
Shape and size of cells: rod, 0.8 μm×1.0 to 1.2 μm
Polymorphism of cells: negative
Mobility: motile
Sporulation: negative
Gram staining: negative
Colony shape: circular; entire, smooth margin; low convex; smooth surface; glossy; cream-colored
(2) Physiological Properties
Catalase: positive
Oxidase: positive
O/F test: oxidative
Nitrate reduction: negative
Indole production: negative
Acid production from glucose: negative
Arginine dihydrolase: negative
Urease: negative
Esculin hydrolysis: negative
Gelatin hydrolysis: negative
β-Galactosidase: negative
Fluorescent pigment production on King's B agar: positive
Growth under 4% NaCl: negative
Poly-β-hydroxybutyrate accumulation: negative
(3) Substrate Assimilation
Glucose: positive
L-Arabinose: negative
D-Mannose: positive
D-Mannitol: positive
N-Acetyl-D-glucosamine: positive
Maltose: negative
Potassium gluconate: positive
n-Caprate: positive
Adipate: negative
dl-Malate: positive
Sodium citrate: positive
Phenyl acetate: positive
Bacteriological Properties of Strain P161
(1) Morphological Properties
Shape and size of cells: sphere, φ0.6 μm, rods, 0.6 μm×1.5 to 2.0 μm
Polymorphism of cells: elongated form
Mobility: motile
Sporulation: negative
Gram staining: negative
Colony shape: circle; entire, smooth margin; low convex; smooth surface; pale yellow
(2) Physiological Properties
Catalase: positive
Oxidase: positive
O/F test: oxidative
Nitrate reduction: positive
Indole production: negative
Acid production from glucose: negative
Arginine dihydrolase: positive
Urease: negative
Esculin hydrolysis: negative
Gelatin hydrolysis: negative
β-Galactosidase: negative
Fluorescent pigment production on King's B agar: positive
(3) Substrate Assimilation
Glucose: positive
L-Arabinose: positive
D-Mannose: positive
D-Mannitol: positive
N-Acetyl-D-glucosamine: positive
Maltose: negative
Potassium gluconate: positive
n-Caprate: positive
Adipate: negative
dl-Malate: positive
Sodium citrate: positive
Phenyl acetate: positive Cultivation According to the PHA production method of the present invention, by culturing the above-mentioned microorganism capable of producing PHA in a culture medium containing ω-[(phenylmethyl)sulfanyl]alkanoic acid represented by the above chemical formula (10) as a feedstock, PHA represented by the chemical formula (1) containing 3-hydroxyalkanate units having a substituted or unsubstituted (phenylmethyl)sulfanyl group at the end of the side chain thereof is produced by and accumulated in the cells.

For ordinary culture of the microorganisms used in the present invention, for example, for preparation of stock strains, or for obtaining cells or maintaining activities required in PHA production, culture media are selected to contain ingredients necessary for the proliferation of the microorganisms used. For example, any one of known culture media, such as typical natural culture media (e.g., nutrient broth, yeast extract) and synthetic culture media supplemented with nutrients, may be used as long as the culture medium does not adversely affect the growth and survival of the microorganisms. Cultivation conditions such as temperature, aeration and agitation are appropriately selected depending on the microorganisms used.

In order to produce the subject PHA by using the PHA-producing microorganism as described above, an inorganic culture medium may be used that contains at least a growth substrate for the microorganism and a compound represented by the above chemical formula (10) corresponding to the monomer unit as the feedstock for PHA production. It is desirable that the compound represented by the above chemical formula (10) be contained in an amount of 0.01% to 1% (w/v), and more preferably 0.02% to 0.2%, per a culture medium. The compound represented by the chemical formula (10) does not always have good water solubility. However, with the microorganisms indicated herein, suspension would cause no trouble.

The feedstock compound represented by the chemical formula (10) may be, in some cases, added to the culture medium as a solution or suspension in a solvent such as 1-hexadecene or n-hexadecane in order to improve dispersibility. In such a case, the concentration of the solvent is required to be equal to or lower than 3% (v/v) relative to the solution of the culture medium.

It is preferable to add a growth substrate for microbial proliferation to the culture medium separately. As the growth substrate, nutrients such as yeast extract, polypeptone, and meat extract may be used. The growth substrate may be selected based on the usefulness as the substrate to the strain to be used, from saccharides, organic acids generated in the TCA cycle, organic acids or salts thereof generated from the biochemical reactions one or two steps later than the TCA cycle, amino acids or salts thereof, $C_4$ to $C_{12}$ straight chain alkanoic acids or salts thereof.

One or more saccharides may suitably be used selected from aldose such as glyceraldehyde, erythrose, arabinose, xylose, glucose, galactose, mannose, and fructose; alditol such as glycerol, erythritol, and xylitol; aldonic acids such as gluconic acid; uronic acid such as glucuronic acid and galacturonic acid; and disaccharide such as maltose, sucrose, and lactose.

As the organic acids or salts thereof, one or more compounds may suitably be selected from pyruvic acid, malic acid, lactic acid, citric acid, succinic acid, and salts thereof.

As the amino acids or salts thereof, one or more compounds may suitably be selected from glutamic acid, aspartic acid, and salts thereof.

Of these, polypeptone and saccharides are preferable. Preferable saccharides include at least one selected from glucose, fructose, and mannose. Preferably, the substrate is contained in an amount of 0.1% to 5% (w/v), and more preferably 0.2% to 2% in the culture medium.

Sometimes the microbial PHA productivity is improved when the microorganism is fully grown and then transferred to a culture medium in which nitrogen source such as ammonium chloride is limited and a compound serving as a substrate for PHA is added. For example, a multi-step approach may be used that performs two or more steps successively under different cultivation conditions.

More specifically, a microorganism is grown in a culture medium that contains a compound represented by the chemical formula (10) and polypeptone until from late logarithmic phase to stationary phase (step 1-1), and then collected by using, for example, centrifugation. Subsequently, the microorganism cultivated in the step 1 is further cultivated in a culture medium that contains a compound represented by the chemical formula (10) and an organic acid or a salt thereof as described above (preferably without a nitrogen source) (step 1-2). Alternatively, the microorganism is cultured in a culture medium that contains a compound represented by the chemical formula (10) and a saccharide as described above until from late logarithmic phase to stationary phase (step 1-3), and collected by using, for example, centrifugation. Subsequently, the microorganism grown in the step 1 is further cultivated in a culture medium that contains the compound represented by the chemical formula (10) and a saccharide as described above (preferably without a nitrogen source) (step 1-4). In the first step of this two-step cultivation procedure, the cells are allowed to proliferate while producing the subject PHA from the feedstock compound represented by the above general formula (10). In the second step, the well-proliferated cells continue PHA production in the culture medium containing no nitrogen source to increase the amount of the PHA accumulated in the cells.

The cultivation temperature should be a temperature at which the above-mentioned strains can proliferate well. For example, the cultivation temperature may be 15° C. to 40° C., preferably 20° C. to 35° C., and more preferably 20° C. to 30° C.

The cultivation may be performed by any suitable cultivation techniques such as liquid or solid cultivation, with which the above-mentioned microorganisms can proliferate to produce polyhydroxyalkanoates. Furthermore, the type of the cultivation is not limited as long as oxygen is supplied properly. Examples include batch cultivation, fed batch cultivation, semi-continuous cultivation, and continuous cultivation. In liquid batch cultivation, the oxygen may be supplied while shaking the content of a shake flask. Alternatively, the oxygen may be supplied by means of an agitation-ventilation method using a jar fermenter.

As the inorganic culture medium to be used for the above-mentioned cultivation procedure, any culture medium may be used that contains ingredients that are required for the proliferation of the microorganisms, such as a phosphorous source (e.g., phosphates) and a nitrogen source (e.g., ammonium salts, nitrates). For example, MSB medium and M9 medium may be used.

The composition of an inorganic culture medium (M9 medium) that is used in a process according to the present invention is given below.

| (M9 Medium) | |
|---|---|
| $Na_2HPO_4$ | 6.2 g |
| $KH_2PO_4$ | 3.0 g |
| NaCl | 0.5 g |
| $NH_4Cl$ | 1.0 g |
| (in 1 liter culture medium; pH 7.0) | |

In order to ensure good proliferation, and production of the polyhydroxyalkanoates, it is necessary to add a trace ingredient solution that is indicated below in an amount of about 0.3% (v/v) to the above-mentioned inorganic culture medium.

(Trace Ingredient Solution)

Nitrilotriacetic Acid: 1.5 g; $MgSO_4$: 3.0 g;

$MnSO_4$: 0.5 g; NaCl: 1.0 g; $FeSO_4$: 0.1 g;

$CaCl_2$: 0.1 g; $CoCl_2$: 0.1 g; $ZnSO_4$: 0.1 g;

$CuSO_4$: 0.1 g; $AlK(SO_4)_2$: 0.1 g;

$H_3BO_3$: 0.1 g; $Na_2MoO_4$: 0.1 g; $NiCl_2$: 0.1 g (1-liter solution; pH 7.0)

PHA Recovery

The microorganism used in the present invention produces and accumulates the subject PHA in the cell. Therefore, in the PHA production process of the present invention, a step of recovering the subject PHA from the cells is provided after the cultivation.

For the purpose of recovering the PHA from the cells, a solvent extraction technique is used, in which a solubilized polyhydroxyalkanoate is separated from insoluble cell components. A standard chloroform extraction technique is the most convenient and simple but a solvent other than chloroform may be used such as dichloromethane, dioxane, tetrahydrofuran, acetonitrile, and acetone.

In environments where it is difficult to use an organic solvent, components of the strains other than the polyhydroxyalkanoates are removed by treating with, for example, a surfactant such as SDS, with an enzyme such as lysozyme, or with EDTA and cellular components are removed to recover only the polyhydroxyalkanoates. Alternatively, one can use cell disruption treatment such as ultrasonic disruption, homogenization, pressure disruption, disruption with glass beads, trituration, grinding and freeze-thawing to separate and recover the polyhydroxyalkanoates accumulated in the cells.

It should be understood that the cultivation of the microorganisms of the present invention, the production of the polyhydroxyalkanoates by the microorganisms of the present invention and accumulation of the polyhydroxyalkanoates in the cell, and the recovery of the polyhydroxyalkanoates from the cell are not limited to the above-mentioned techniques and procedures.

The polyhydroxyalkanoates that are produced by the microorganisms according to the process of the present invention may comprise, in addition to the units represented by the chemical formula (1), 3-hydroxyalkanoic acid units represented by the chemical formula (4) or 3-hydroxyalk-5-enoic acid units represented by the chemical formula (5) that is biosynthesized through a fatty acid synthesizing system by using a proliferation substrate to be added to the culture medium. The carbons at the 3 position of all 3-hydroxyalkanoic acid units contained are asymmetric carbons whose absolute configuration is R, indicating the biodegradability thereof. The presence of the (phenylmethyl)sulfanyl group in the units represented by the chemical formula (1) and the presence of the various substituents positioned on the benzene ring thereof provide new physical and chemical properties to the polymers. Improvements in physical properties of such polymers are expected. The polymers can be expanded to the fields to which they were not applicable in the past.

EXAMPLES

The present invention is described specifically below with reference to examples thereof, but not limited thereto. In the following examples, percentages are by weight unless otherwise specified.

Example 1

*Pseudomonas cichorii* YN2 was inoculated to 200 mL of M9 medium containing 0.5% of D-glucose and 0.1% of 5-[(phenylmethyl)sulfanyl]valeric acid, and cultured with shaking at 125 strokes/min at 30° C. for 48 hours. Then, the cells were collected by centrifugation, re-suspended in 200 mL of M9 medium containing 0.5% of D-glucose and 0.1% of 5-[(phenylmethyl)sulfanyl]valeric acid but no nitrogen source ($NH_4Cl$), and cultured at 30° C. with shaking at 125 strokes/min for 48 hours. After that, the cells were collected by centrifugation, washed once with cold methanol, and lyophilized.

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 159 mg of polyhydroxyalkanoate.

The polyhydroxyalkanoate was subjected to NMR analysis under the following conditions.

Figure 2:
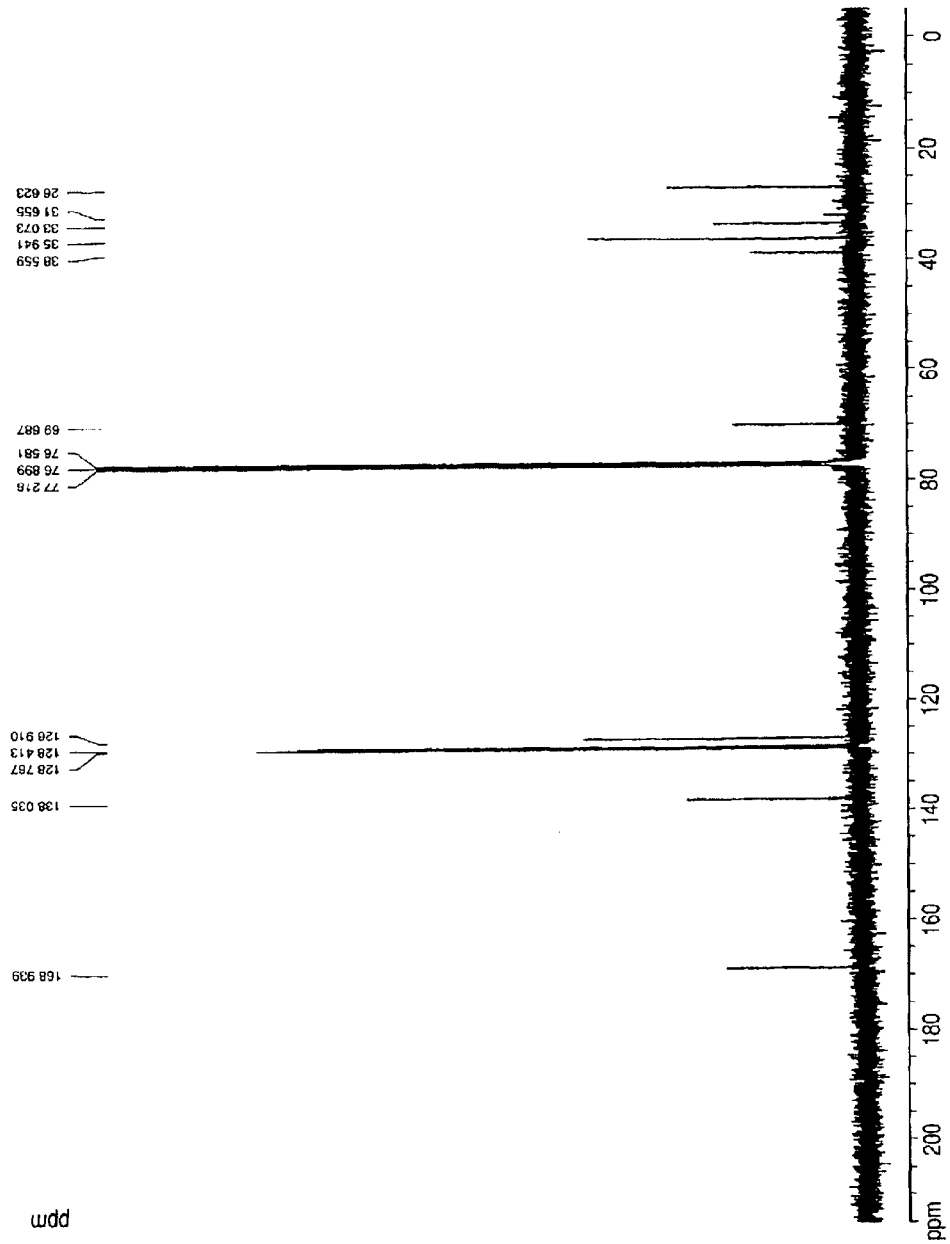
FIG. 2 shows the $^{13}C$ NMR spectrum of the polyhydroxyalkanoate obtained in the Example 1.

Spectrometer
FT-NMR: Bruker DPX 400 with spectrometer frequencies of 400 MHz for $^1$H-NMR and 100 MHz for $^{13}$C.
Conditions
Nuclear Species: $^1$H, $^{13}$C
Solvent: $CDCl_3$
Temperature: room temperature
FIGS. 1 and 2 show $^1$H-NMR spectra and $^{13}$C-NMR spectra, respectively, of the polyhydroxyalkanoate. Identification results thereof are given in Tables 1 and 2 below.

TABLE 1

| Chemical shifts (ppm) | Integration | Splitting patterns | Identification |
|---|---|---|---|
| 1.83 | 2 H | qurt | d1 |
| 2.36–2.54 | 4 H | m | b1, c1 |
| 3.67 | 2 H | s | f1 |
| 5.20 | 1 H | quint | c1 |
| 7.20 | 1 H | m | j1 |
| 7.25–7.28 | 4 H | m | h1, l1 & i1, k1 |

TABLE 2

| Chemical shifts (ppm) | Identification |
|---|---|
| 26.6 | d1 |
| 33.0 | e1 |
| 35.9 | f1 |
| 38.6 | b1 |
| 69.7 | c1 |
| 126.9 | j1 |
| 128.4 | h, l |
| 128.8 | i, k |
| 138.0 | g1 |
| 168.9 | a1 |

As clearly shown by Tables 1 and 2, it was confirmed that the polyhydroxyalkanoate is one represented by the following chemical formula (16) containing, as the monomer units, 3-hydroxy-5-[(phenylmethyl)sulfanyl]valerate, and 3-hydroxyalkanoates and/or 3-hydroxyalkenoates corresponding to saturated/unsaturated fatty acids having 4 to 12 carbon atoms such as 3-hydroxybutyric acid and 3-hydroxyvaleric acid. The integration of the $^1$H-NMR spectra indicated that the polyhydroxyalkanoate contains 3-hydroxy-5-[(phenylmethyl)sulfanyl]valerate by 85.9 mol %.

(16)

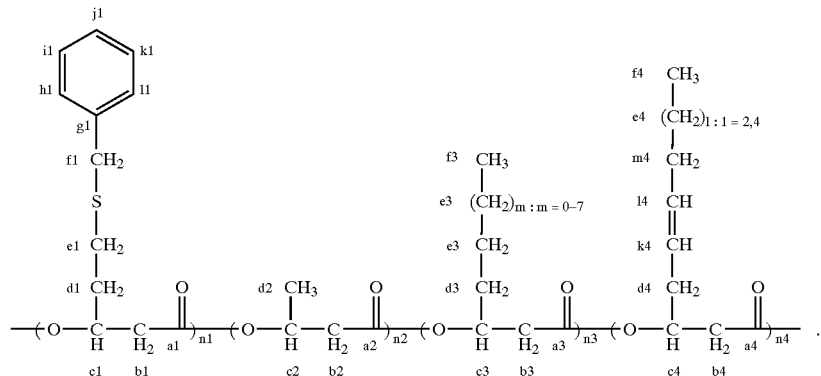

The molecular weight of the polyhydroxyalkanoate was determined by gel permeation chromatography (GPC;

TOSOH HLC-8220, column; TOSOH TSK-GEL SuperHM-H (trade name), solvent; chloroform, polystyrene equivalent). As a result, Mn was 14,400 and Mw was 56,700.

Example 2

Pseudomonas cichorii H45 was inoculated to 200 mL of M9 medium containing 0.5% of D-glucose and 0.1% of 5-[(phenylmethyl)sulfanyl]valeric acid, and cultured with shaking at 125 strokes/min at 30° C. for 48 hours. Then, the cells were collected by centrifugation, re-suspended in 200 mL of M9 medium containing 0.5% of D-glucose and 0.1% of 5-[(phenylmethyl)sulfanyl]valeric acid but no nitrogen source ($NH_4Cl$), and cultured at 30° C. with shaking at 125 strokes/min for 48 hours. After that, the cells were collected by centrifugation, washed once with cold methanol, and lyophilized.

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 138 mg of polyhydroxyalkanoate.

The polyhydroxyalkanoate obtained was subjected to NMR analysis under the same conditions as in the Example 1. As a result, it was revealed that this polyhydroxyalkanoate is one represented by the chemical formula (16) containing, as the monomer units, 3-hydroxy-5-[(phenylmethyl)sulfanyl]valerate, and 3-hydroxyalkanoates and/or 3-hydroxyalkenoates corresponding to saturated/unsaturated fatty acids having 4 to 12 carbon atoms such as 3-hydroxybutyric acid and 3-hydroxyvaleric acid. The integration of the $^1$H-NMR spectra indicated that the polyhydroxyalkanoate contains 3-hydroxy-5-[(phenylmethyl)sulfanyl]valerate by 95.2 mol %.

Example 3

Pseudomonas jessenii P161 was inoculated to 200 lb mL of M9 medium containing 0.5% of D-glucose and 0.1% of 5-[(phenylmethyl)sulfanyl]valeric acid, and cultured with shaking at 125 strokes/min at 30° C. for 48 hours. Then, the cells were collected by centrifugation, re-suspended in 200 mL of M9 medium containing 0.5% of D-glucose and 0.1% of 5-[(phenylmethyl)sulfanyl]valeric acid but no nitrogen source ($NH_4Cl$), and cultured at 30° C. with shaking at 125 strokes/min for 47 hours. After that, the cells were collected by centrifugation, washed once with cold methanol, and lyophilized.

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 164 mg of polyhydroxyalkanoate.

The polyhydroxyalkanoate obtained was subjected to NMR analysis under the same conditions as in the Example 1. As a result, it was revealed that this polyhydroxyalkanoate is one represented by the chemical formula (16) containing, as the monomer units, 3-hydroxy-5-[(phenylmethyl)sulfanyl]valerate, and 3-hydroxyalkanoates and/or 3-hydroxyalkenoates corresponding to saturated/unsaturated fatty acids having 4 to 12 carbon atoms such as 3-hydroxybutyric acid and 3-hydroxyvaleric acid. The integration of the $^1$H-NMR spectra indicated that the polyhydroxyalkanoate contains 3-hydroxy-5-[(phenylmethyl)sulfanyl]valerate by 96.7 mol %.

Example 4

Pseudomonas cichorii YN2 was inoculated to 200 mL of M9 medium containing 0.5% of polypeptone (Wako Pure Chemical Industries, Ltd.) and 0.1% of 5-[(phenylmethyl)sulfanyl]valeric acid, and cultured with shaking at 125 strokes/min at 30° C. for 48 hours. Then, the cells were collected by centrifugation, washed once with cold methanol, and lyophilized.

The lyophilized pellet was suspended in 20 ml of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 161 mg of polyhydroxyalkanoate.

The polyhydroxyalkanoate obtained was subjected to NMR analysis under the same conditions as in the Example 1. As a result, it was revealed that this polyhydroxyalkanoate is one represented by the chemical formula (16) containing, as the monomer units, 3-hydroxy-5-[(phenylmethyl)sulfanyl]valerate, and 3-hydroxyalkanoates and/or 3-hydroxyalkenoates corresponding to saturated/unsaturated fatty acids having 4 to 12 carbon atoms such as 3-hydroxybutyric acid and 3-hydroxyvaleric acid. The integration of the $^1$H-NMR spectra indicated that the polyhydroxyalkanoate contains 3-hydroxy-5-[(phenylmethyl)sulfanyl]valerate by 83.8 mol %.

Example 5

Pseudomonas cichorii H45 was inoculated to 200 mL of M9 medium containing 0.5% of polypeptone (Wako Pure Chemical Industries, Ltd.) and 0.1% of 5-[(phenylmethyl)sulfanyl]valeric acid, and cultured with shaking at 125 strokes/min at 30° C. for 48 hours. Then, the cells were collected by centrifugation, washed once with cold methanol, and lyophilized.

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 113 mg of polyhydroxyalkanoate.

The polyhydroxyalkanoate obtained was subjected to NMR analysis under the same conditions as in the Example 1. As a result, it was revealed that this polyhydroxyalkanoate is one represented by the chemical formula (16) containing, as the monomer units, 3-hydroxy-5-[(phenylmethyl)sulfanyl]valerate, and 3-hydroxyalkanoates and/or 3-hydroxyalkenoates corresponding to saturated/unsaturated fatty acids having 4 to 12 carbon atoms such as 3-hydroxybutyric acid and 3-hydroxyvaleric acid. The integration of the $^1$H-NMR spectra indicated that the polyhydroxyalkanoate contains 3-hydroxy-5-[(phenylmethyl)sulfanyl]valerate by 96.2 mol %.

Example 6

Pseudomonas jessenii P161 was inoculated to 200 mL of M9 medium containing 0.5% of polypeptone (Wako Pure Chemical Industries, Ltd.) and 0.1% of 5-[(phenylmethyl)sulfanyl]valeric acid, and cultured with shaking at 125 strokes/min at 30° C. for 48 hours. Then, the cells were collected by centrifugation, washed once with cold methanol, and lyophilized.

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 126 mg of polyhydroxyalkanoate.

The polyhydroxyalkanoate obtained was subjected to NMR analysis under the same conditions as in the Example 1. As a result, it was revealed that this polyhydroxyalkanoate is one represented by the chemical formula (16) containing, as the monomer units, 3-hydroxy-5-[(phenylmethyl) sulfanyl]valerate, and 3-hydroxyalkanoates and/or 3-hydroxyalkenoates corresponding to saturated/unsaturated fatty acids having 4 to 12 carbon atoms such as 3-hydroxybutyric acid and 3-hydroxyvaleric acid. The integration of the $^1$H-NMR spectra indicated that the polyhydroxyalkanoate contains 3-hydroxy-5-[(phenylmethyl) sulfanyl]valerate by 89.8 mol %.

Example 7

*Pseudomonas cichorii* YN2 was inoculated to 200 mL of M9 medium containing 0.1% of nonanoic acid and 0.1% of 5-[(phenylmethyl)sulfanyl]valeric acid, and cultured with shaking at 125 strokes/min at 30° C. for 48 hours. Then, the cells were collected by centrifugation, washed once with cold methanol, and lyophilized.

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 90 mg of polyhydroxyalkanoate.

The polyhydroxyalkanoate obtained was subjected to NMR analysis under the same conditions as in the Example 1. As a result, it was revealed that this polyhydroxyalkanoate is one represented by the chemical formula (16) containing, as the monomer units, 3-hydroxy-5-[(phenylmethyl) sulfanyl]valerate, and 3-hydroxyalkanoates and/or 3-hydroxyalkenoates corresponding to saturated/unsaturated fatty acids having 4 to 12 carbon atoms such as 3-hydroxybutyric acid and 3-hydroxyvaleric acid. The integration of the $^1$H-NMR spectra indicated that the polyhydroxyalkanoate contains 3-hydroxy-5-[(phenylmethyl) sulfanyl]valerate by 29.2 mol %.

Example 8

*Pseudomonas cichorii* YN2 was inoculated to 200 mL of M9 medium containing 0.5% of yeast extract, and 0.1% of 5-[(phenylmethyl)sulfanyl]valeric acid, and cultured with shaking at 125 strokes/min at 30° C. for 48 hours. Then, the cells were collected by centrifugation, washed once with cold methanol, and lyophilized.

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 103 mg of polyhydroxyalkanoate.

The polyhydroxyalkanoate obtained was subjected to NMR analysis under the same conditions as in the Example 1. As a result, it was revealed that this polyhydroxyalkanoate is one represented by the chemical formula (16) containing, as the monomer units, 3-hydroxy-5-[(phenylmethyl) sulfanyl]valerate, and 3-hydroxyalkanoates and/or 3-hydroxyalkenoates corresponding to saturated/unsaturated fatty acids having 4 to 12 carbon atoms such as 3-hydroxybutyric acid and 3-hydroxyvaleric acid. The integration of the $^1$H-NMR spectra indicated that the polyhydroxyalkanoate contains 3-hydroxy-5-[(phenylmethyl) sulfanyl]valerate by 96.0 mol %.

Example 9

*Pseudomonas cichorii* YN2 was inoculated to 200 mL of M9 medium containing 0.5% of sodium glutamate and 0.1% of 5-[(phenylmethyl)sulfanyl]valeric acid, and cultured with shaking at 125 strokes/min at 30° C. for 48 hours. Then, the cells were collected by centrifugation, washed once with cold methanol, and lyophilized.

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 87 mg of polyhydroxyalkanoate.

The polyhydroxyalkanoate obtained was subjected to NMR analysis under the same conditions as in the Example 1. As a result, it was revealed that this polyhydroxyalkanoate is one represented by the chemical formula (16) containing, as the monomer units, 3-hydroxy-5-[(phenylmethyl) sulfanyl]valerate, and 3-hydroxyalkanoates and/or 3-hydroxyalkenoates corresponding to saturated/unsaturated fatty acids having 4 to 12 carbon atoms such as 3-hydroxybutyric acid and 3-hydroxyvaleric acid. The integration of the $^1$H-NMR spectra indicated that the polyhydroxyalkanoate contains 3-hydroxy-5-[(phenylmethyl) sulfanyl]valerate by 86.4 mol %.

Table 3 shows the dry weight of the cells, the dry weight of the polymer, the ratio of the polymer to the cells by dry weight, and the amount (mol %) of the 3-hydroxy-5-[(phenylmethyl)sulfanyl]valerate (abbreviated as "3HBzyTV") unit in the resulting polymer in Examples 1–9.

TABLE 3

|  | Cell Dry Weight (mg/L) | Polymer Dry Weight (mg/L) | Polymer Weight/ Cell Weight (%) | 3HBzyTV Unit mol % |
|---|---|---|---|---|
| Example 1 | 1070 | 795 | 74.3 | 85.9 |
| Example 2 | 875 | 690 | 78.9 | 95.2 |

TABLE 3-continued

| | Cell Dry Weight (mg/L) | Polymer Dry Weight (mg/L) | Polymer Weight/ Cell Weight (%) | 3HBzyTV Unit mol % |
|---|---|---|---|---|
| Example 3 | 1015 | 820 | 80.8 | 96.7 |
| Example 4 | 1070 | 805 | 75.2 | 83.8 |
| Example 5 | 710 | 565 | 79.6 | 96.2 |
| Example 6 | 940 | 630 | 67.0 | 89.8 |
| Example 7 | 705 | 450 | 63.8 | 29.2 |
| Example 8 | 815 | 515 | 63.2 | 96.0 |
| Example 9 | 995 | 435 | 43.7 | 86.4 |

Example 10

Process for Producing Polyhydroxyalkanoate Containing 3-Hydroxy-4-[(Phenylmethyl)sulfanyl] Butyrate Monomer Unit

*Pseudomonas cichorii* YN2 was inoculated to 200 mL of M9 medium containing 0.5% of yeast extract and 0.1% of 4-[(phenylmethyl)sulfanyl]butyric acid, and cultured at 30° C. with shaking at 125 strokes/min for 48 hours. Then, the cells were collected by centrifugation, washed once with cold methanol, and lyophilized. The weight of the lyophilized cells (dry weight of the cells) was weighed.

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 39 mg of polyhydroxyalkanoate.

The average molecular weight of the resulting PHA was determined by gel permeation chromatography (GPC: TOSOH HLC-8220 (trade name), column: TOSOH TSK-GEL SuperHM-H (trade name), solvent: chloroform, polystyrene equivalent). As a result, the number average molecular weight Mn was 44,500 and the weight average molecular weight Mw was 106,800.

In order to identify the structure of the PHA obtained, the PHA was subjected to NMR analysis under the following conditions.

Figure 3:
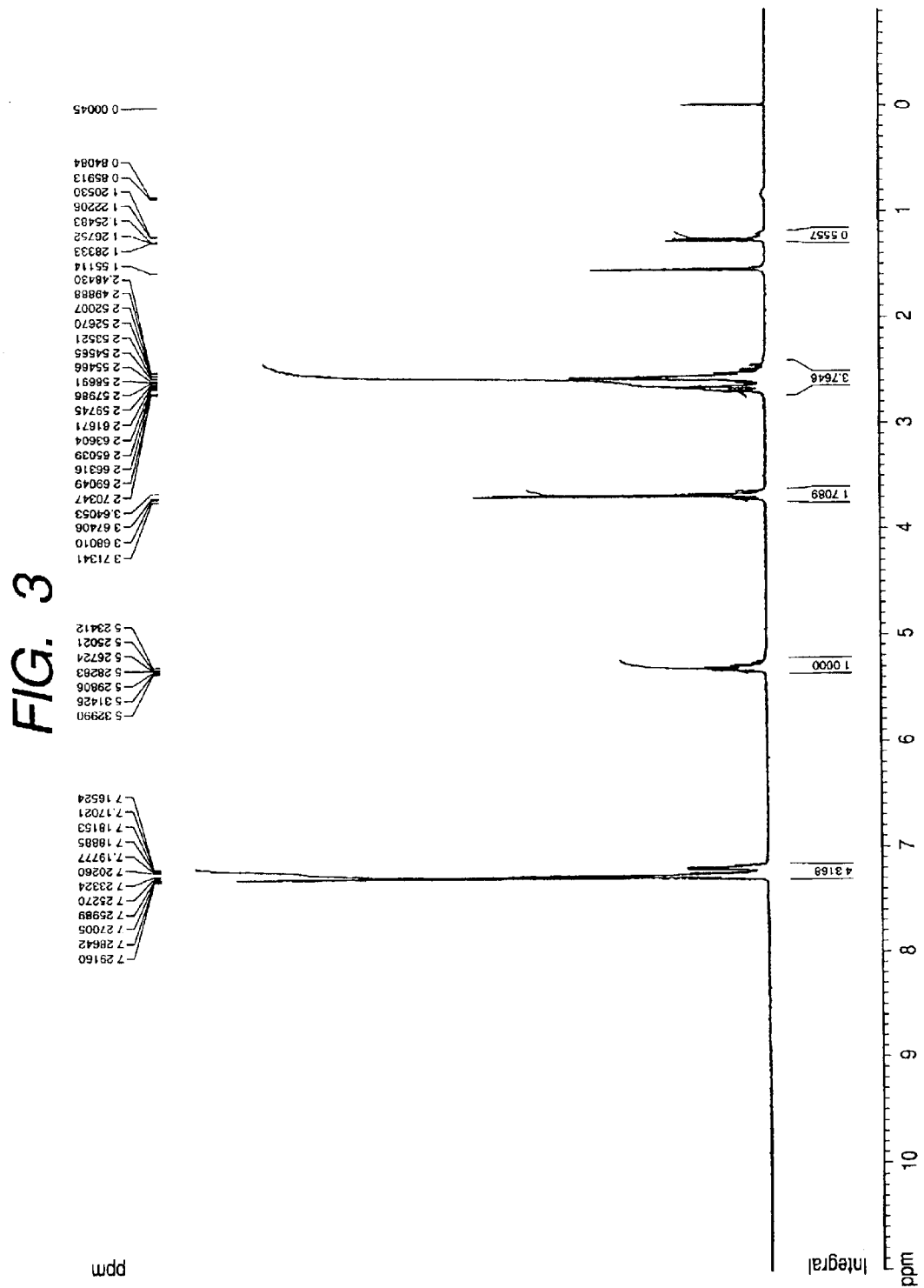
FIG. 3 shows the $^1H$ NMR spectrum of a polyhydroxyalkanoate obtained in Example 10.

Spectrometer
FT-NMR: Bruker DPX 400 with spectrometer frequency of 400 MHz for $^1$H-NMR.
Conditions
 Nuclear Species: $^1$H
 Solvent: CDCl$_3$
Reference: TMS/CDCl$_3$ in capillary
Temperature: room temperature FIG. 3 shows measured $^1$H-NMR spectra and identification results thereof are given in Table 4 below.

TABLE 4

| Chemical shift (ppm) | Integration | Splitting pattern | Identification |
|---|---|---|---|
| 2.48–2.71 | 4 H | m | B5, d5 |
| 3.68 | 2 H | m | e5 |
| 5.27 | 1 H | m | c5 |
| 7.18 | 1 H | m | i5 |
| 7.25 | 4 H | m | g5, k5, h5, j5 |

The results shown in the Table 4 confirm that this polyhydroxyalkanoate contains as the monomer units, 3-hydroxy-4-[(phenylmethyl)sulfanyl]butyrate, and 3-hydroxyalkanoates and/or 3-hydroxyalkenoates corresponding to saturated/unsaturated fatty acids having 4 to 12 carbon atoms such as 3-hydroxybutyric acid or 3-hydroxyvaleric acid. More specifically, the PHA has a structure represented by the following chemical formula (17):

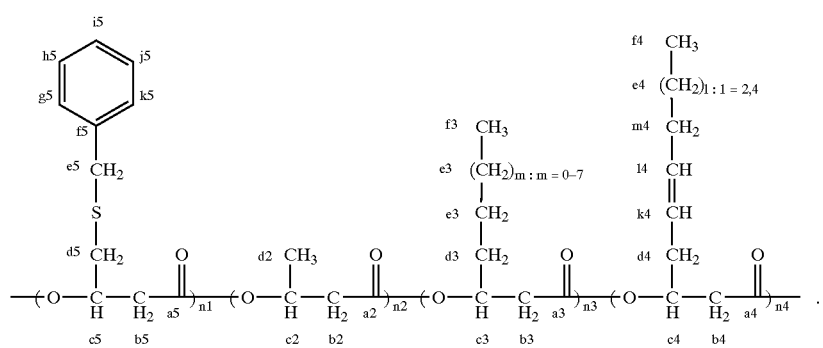

(17)

The integration of the $^1$H-NMR spectra indicated that the polyhydroxyalkanoate contains 3-hydroxy-4-[(phenylmethyl)sulfanyl]butyrate by 85.4 mol %.

Example 11

*Pseudomonas cichorii* YN2 was inoculated to 200 mL of M9 medium containing 0.1% of nonanoic acid and 0.1% of 4-[(phenylmethyl)sulfanyl]butyric acid, and cultured at 30° C. with shaking at 125 strokes/min for 48 hours. Then, the cells were collected by centrifugation, washed once with cold methanol, and lyophilized. The weight of the lyophilized cells was measured (dry weight of the cells).

The lyophilized pellet was suspended in 20 mL, of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 68 mg of polyhydroxyalkanoate.

The polyhydroxyalkanoate obtained was subjected to NMR analysis under the same conditions as in the Example 10. As a result, it was revealed that this polyhydroxyalkanoate is one represented by the chemical formula (17) containing a monomer unit of 3-hydroxy-4-[(phenylmethyl) sulfanyl]butyrate, and other monomer units of 3-hydroxyalkanoates and/or 3-hydroxyalkenoates corresponding to saturated/unsaturated fatty acids having 4 to 12 carbon atoms such as 3-hydroxybutyric acid or 3-hydroxyvaleric acid. The integration of the $^1$H-NMR spectra indicated that the polyhydroxyalkanoate contains 3-hydroxy-4-[(phenylmethyl)sulfanyl]butyrate by 27.7 mol %.

Example 12

Pseudomonas cichorii YN2 was inoculated to 200 mL of M9 medium containing 0.5% of sodium glutamate and 0.1% of 4-[(phenylmethyl)sulfanyl]butyric acid, and cultured at 30° C. with shaking at 125 strokes/min for 48 hours. Then, the cells were collected by centrifugation, washed once with cold methanol, and lyophilized. The weight of the lyophilized cells was weighed (dry weight of the cells).

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 72 mg of polyhydroxyalkanoate.

The polyhydroxyalkanoate obtained was subjected to NMR analysis under the conditions as set forth in the Example 10. As a result, it was revealed that this polyhydroxyalkanoate is one represented by the chemical formula (17). The polyhydroxyalkanoate comprises a monomer unit of 3-hydroxy-4-[(phenylmethyl)sulfanyl]butyrate and other monomer units of 3-hydroxyalkanoates and/or 3-hydroxyalkenoates having 4 to 12 carbon atoms such as 3-hydroxybutyrate and 3-hydroxyvaleric acid. The integration of the $^1$H-NMR spectra indicated that the resulting polyhydroxyalkanoate contains 50.3 mol % of 3-hydroxy-4-[(phenylmethyl)sulfanyl]butyrate monomer unit.

Example 13

Pseudomonas cichorii YN2 was inoculated to 200 mL of M9 medium containing 0.5% of D-glucose and 0.1% of 4-[(phenylmethyl)sulfanyl]butyric acid, and cultured with shaking at 125 strokes/min at 30° C. for 48 hours. Then, the cells were collected by centrifugation, re-suspended in 200 mL of M9 medium containing 0.5% of D-glucose and 0.1% of 4-[(phenylmethyl)sulfanyl]butyric acid but no nitrogen source (NH$_4$Cl), and cultured at 30° C. with shaking at 125 strokes/min for 48 hours. After that, the cells were collected by centrifugation, washed once with cold methanol, and lyophilized. The lyophilized cells were weighed (cell dry weight).

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 148 mg of polyhydroxyalkanoate.

The polyhydroxyalkanoate obtained was subjected to NMR analysis under the conditions as set forth in the Example 10. As a result, it was revealed that this polyhydroxyalkanoate is the polyhydroxyalkanoate that is represented by the chemical formula (17). The polyhydroxyalkanoate comprises a monomer unit of 3-hydroxy-4-[(phenylmethyl)sulfanyl]butyrate and other monomer units of 3-hydroxyalkanoicates and/or 3-hydroxyalkenoates having 4 to 12 carbon atoms such as 3-hydroxybutyrate and 3-hydroxyvalerate. The integration of the $^1$H-NMR spectra indicated that the resulting polyhydroxyalkanoate contains 66.7 mol % of the 3-hydroxy-4-[(phenylmethyl)sulfanyl] butyrate monomer unit.

Example 14

Pseudomonas cichorii H45 was inoculated to 200 mL of N9 medium containing 0.5% of polypeptone (Wako Pure Chemical Industries, Ltd.) and 0.1% of 5-[(phenylmethyl)sulfanyl]butyric acid, and cultured with shaking at 125 strokes/min at 30° C. for 48 hours. Then, the cells were collected by centrifugation, washed once with cold methanol, and lyophilized. The weight of the lyophilized cells was weighed (dry weight of the cells).

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 20 mg of polyhydroxyalkanoate.

The polyhydroxyalkanoate obtained was subjected to NMR analysis under the conditions as set forth in the Example 10. As a result, it was revealed that this polyhydroxyalkanoate is one represented by the chemical formula (17). The polyhydroxyalkanoate comprises a monomer unit of 3-hydroxy-4-[(phenylmethyl)sulfanyl]butyrate and other monomer units of 3-hydroxyalkanoates and/or 3-hydroxyalkenoates corresponding to saturated/unsaturated fatty acids having 4 to 12 carbon atoms such as 3-hydroxybutyric acid and 3-hydroxyvaleric acid. The integration of the $^1$H-NMR spectra indicated that the resulting polyhydroxyalkanoate contains 57.2 mol % of 3-hydroxy-4-[(phenylmethyl)sulfanyl]butyrate monomer unit.

Example 15

Pseudomonas jessenii P161 was inoculated to 200 mL of M9 medium containing 0.5% of D-glucose and 0.1% of 5-[(phenylmethyl)sulfanyl]valeric acid, and cultured with shaking at 125 strokes/min at 30° C. for 48 hours. Then, the cells were collected by centrifugation, re-suspended in 200 mL of M9 medium containing 0.5% of D-glucose and 0.1% of 5-[(phenylmethyl)sulfanyl]valeric acid but no nitrogen source (NH$_4$Cl), and cultured at 30° C. with shaking at 125 strokes/min for 48 hours. After that, the cells were collected by centrifugation, washed once with cold methanol, and lyophilized. The weight of the lyophilized cells was weighed (the cell dry weight).

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 64 mg of polyhydroxyalkanoate.

The polyhydroxyalkanoate obtained was subjected to NMR analysis under the conditions as set forth in the Example 10. As a result, it was revealed that this polyhydroxyalkanoate is one represented by the chemical formula (17). The polyhydroxyalkanoate comprises a monomer unit of 3-hydroxy-4-[(phenylmethyl)sulfanyl]butyrate and other monomer units of 3-hydroxyalkanoates and/or 3-hydroxyalkenoates corresponding to saturated/unsaturated fatty acids having 4 to 12 carbon atoms such as 3-hydroxybutyric acid and 3-hydroxyvaleric acid. The integration of the $^1$H-NMR spectra indicated that the resulting polyhydroxyalkanoate contains 31.6 mol % of 3-hydroxy-4-[(phenylmethyl)sulfanyl]butyrate monomer unit.

Table 5 shows the dry weight of the cells, the dry weight of the polymer, the dry weight ratio of the polymer to the cells, and the amount (mol %) of 3-hydroxy-4-[(phenylmethyl)sulfanyl]butyrate (abbreviated as "3HBzyTB" units) in the resulting polymer in Examples 10–15.

TABLE 5

| | Cell Dry Weight (mg/L) | Polymer Dry Weight (mg/L) | Polymer Weight/ Cell Weight (%) | 3HBzyTB Unit mol % |
|---|---|---|---|---|
| Example 10 | 1040 | 195 | 18.8 | 85.4 |
| Example 11 | 655 | 340 | 51.9 | 27.7 |
| Example 12 | 955 | 360 | 37.7 | 50.3 |
| Example 13 | 1370 | 740 | 54.0 | 66.7 |
| Example 14 | 580 | 100 | 17.2 | 57.2 |
| Example 15 | 915 | 320 | 35.0 | 31.6 |

Process for Producing Polyhydroxyalkanoate containing 3-Hydroxy-5-{[(4-Methylphenyl)methyl] Sulfanyl} Valerate Monomer Unit Example 16

*Pseudomonas cichorii* YN2 was inoculated to 200 mL of M9 medium containing 0.5% of D-glucose and 0.1% of 5-[[(4-methylphenyl)methyl]sulfanyl]valeric acid, and cultured with shaking at 125 strokes/min at 30° C. for 48 hours. Then, the cells were collected by centrifugation, re-suspended in 200 mL of M9 medium containing 0.5% of D-glucose and 0.1% of 5-[[4-methylphenyl)methyl] sulfanyl]valeric acid but no nitrogen source (NH$_4$Cl), and cultured at 30° C. with shaking at 125 strokes/min for 48 hours. After that, the cells were collected by centrifugation, washed once with cold methanol, and lyophilized.

The lyophilized pellet was suspended in 20 mL of chloroform and stirred at 60° C. for 20 hours to extract polyhydroxyalkanoate. The extract was filtered through a membrane filter of a pore size of 0.45 µm and concentrated by a rotary evaporator. The concentrated solution was precipitated with cold methanol. The precipitate was recovered and dried in vacuum to yield 96 mg of polyhydroxyalkanoate.

The polyhydroxyalkanoate obtained was subjected to NMR analysis under the conditions as set forth in Example 10. As a result, it was revealed that this polyhydroxyalkanoate is one represented by the chemical formula (18). The polyhydroxyalkanoate comprises a monomer unit of 3-hydroxy-5-[[(4-methylphenyl)methyl]sulfanyl]valerate and other monomer units of 3-hydroxyalkanoates and/or 3-hydroxyalkenoates corresponding to saturated/unsaturated fatty acids having 4 to 12 carbon atoms such as 3-hydroxybutyric acid and 3-hydroxyvaleric acid. The integration of the $^1$H-NMR spectra indicated that the resulting polyhydroxyalkanoate contains 41.0 mol % of 3-hydroxy-5-{[(4-methylphenyl)methyl]sulfanyl}valerate monomer unit.

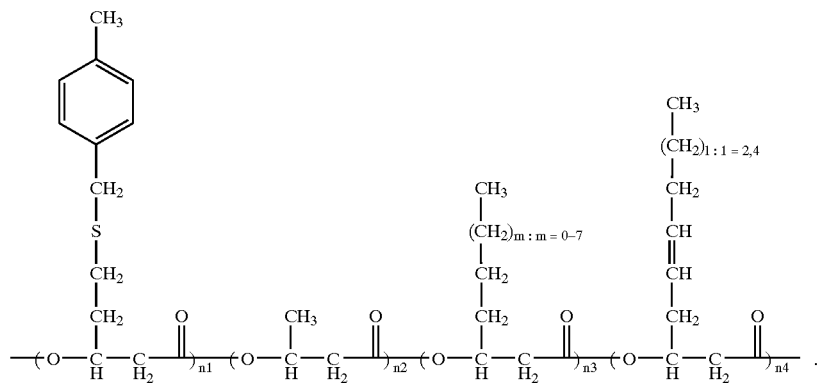

(18)

The molecular weight of the resulting polyhydroxyalkanoate was determined by gel permeation chromatography (GPC; TOSOH HLC-8220, column; TOSOH TSK-GEL SuperHM-H, solvent; chloroform, polystyrene equivalent). As a result, Mn was 21,500 and Mw was 83,200.

Example 17

*Pseudomonas cichorii* H45 was inoculated to 200 mL of M9 medium containing 0.5% of D-glucose and 0.1% of 5-[[(4-methylphenyl)methyl)sulfanyl]valeric acid, and cultured with shaking at 125 strokes/min at 30° C. for 48 hours. Then, the cells were collected by centrifugation, re-suspended in 200 mL of M9 medium containing 0.5% of D-glucose and 0.1% of 5-[[4-methylphenyl)methyl] sulfanyl]valeric acid but no nitrogen source (NH$_4$Cl), and cultured at 30° C. with shaking at 125 strokes/min for 48 hours. After that, the cells were collected by centrifugation, washed once with cold methanol, and lyophilized.

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 82 mg of polyhydroxyalkanoate.

The polyhydroxyalkanoate obtained was subjected to NMR analysis under the conditions as set forth in Example 10. As a result, it was revealed that this polyhydroxyalkanoate is one represented by the chemical formula (18). The polyhydroxyalkanoate comprises a monomer unit of 3-hydroxy-5-[[(4-methylphenyl)methyl]sulfanyl]valerate and other monomer units of 3-hydroxyalkanoates and/or 3-hydroxyalkenoates corresponding to saturated/unsaturated fatty acids having 4 to 12 carbon atoms such as 3-hydroxybutyric acid and 3-hydroxyvaleric acid. The integration of the $^1$H-NMR spectra indicated that the resulting polyhydroxyalkanoate contains 56.2 mol % of 3-hydroxy-5-[[(4-methylphenyl)methyl]sulfanyl]valerate monomer unit.

Example 18

Pseudomonas jessenii P161 was inoculated to 200 mL of M9 medium containing 0.5% of D-glucose and 0.1% of 5-[[(4-methylphenyl)methyl]sulfanyl]valeric acid, and cultured with shaking at 125 strokes/min at 30° C. for 48 hours. Then, the cells were collected by centrifugation, re-suspended in 200 mL of M9 medium containing 0.5% of D-glucose and 0.1% of 5-[[4-methylphenyl)methyl] sulfanyl]valeric acid but no nitrogen source ($NH_4Cl$), and cultured at 30° C. with shaking at 125 strokes/min for 48 hours. After that, the cells were collected by centrifugation, washed once with cold methanol, and lyophilized.

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 75 mg of polyhydroxyalkanoate.

The polyhydroxyalkanoate obtained was subjected to NMR analysis under the conditions as set forth in Example 10. As a result, it was revealed that this polyhydroxyalkanoate is one represented by the chemical formula (18). The polyhydroxyalkanoate comprises a monomer unit of 3-hydroxy-5-[[(4-methylphenyl)methyl]sulfanyl]valerate and other monomer units of 3-hydroxyalkanoates and/or 3-hydroxyalkenoates corresponding to saturated/unsaturated fatty acids having 4 to 12 carbon atoms such as 3-hydroxybutyric acid and 3-hydroxyvaleric acid. The integration of the $^1$H-NMR spectra indicated that the resulting polyhydroxyalkanoate contains 38.8 mol % of 3-hydroxy-5-{[(4-methylphenyl)methyl]sulfanyl}valerate monomer unit.

Table 6 shows the dry weight of the cells, the dry weight of the polymer, the dry weight ratio of the polymer to the cells, and the amount (mol %) of the 3-hydroxy-3-hydroxy-5-{[(4-methylphenyl)methyl]sulfanyl)valerate (abbreviated as "3HMBzyTV" in the resulting polymer in Examples 16–18.

TABLE 6

| | Cell Dry Weight (mg/L) | Polymer Dry Weight (mg/L) | Polymer Weight/ Cell Weight (%) | 3HMBzyTV Unit mol % |
|---|---|---|---|---|
| Example 16 | 805 | 481 | 59.8 | 41.0 |
| Example 17 | 625 | 408 | 65.3 | 56.2 |
| Example 18 | 710 | 377 | 53.1 | 38.8 |

Example 19

Pseudomonas cichorii YN2 was inoculated to 200 mL of M9 medium containing 0.5% of polypeptone (Wako Pure Chemical Industries, Ltd.) and 0.1% of 5-{[(4-fluorophenyl)methyl]sulfanyl}valeric acid, and cultured with shaking at 125 strokes/min at 30° C. for 48 hours. Then, the cells were collected by centrifugation, washed once with cold methanol, and lyophilized. The weight of the lyophilized cells was weighed (dry weight of the cells).

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The sole precipitate was recovered and dried in vacuum to yield 106 mg of polyhydroxyalkanoate.

The average molecular weight of the resulting PHA was determined by gel permeation chromatography (GPC; TOSOH HLC-8220, column; TOSOH TSK-GEL SuperHM-H, solvent; chloroform, polystyrene equivalent). As a result, the number average molecular weight Mn was 32,000 and the weight average molecular weight Mw was 96,000.

In order to identify the structure of the PHA obtained, the PHA was subjected to NMR analysis under the following conditions.

Spectrometer

FT-NMR: Bruker DPX 400 with spectrometer frequencies of 400 MHz for $^1$H-NMR and 100 MHz for $^{13}$C-NMR.

Conditions

Nuclear Species: $^1$H, $^{13}$C Solvent: $CDCl_3$

Temperature: room temperature

Figure 4:
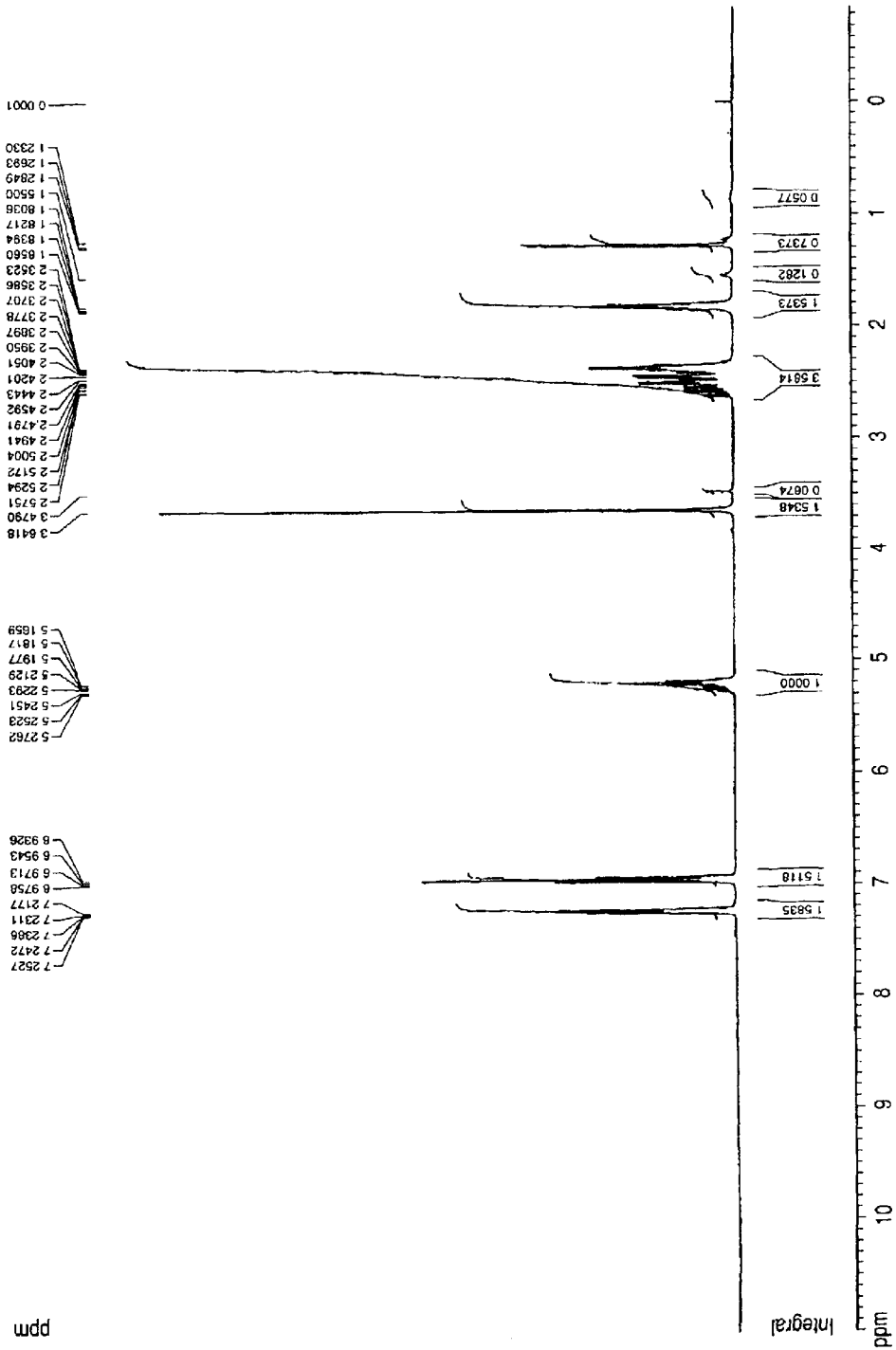
FIG. 4 shows the $^1H$ NMR spectrum of a PHA obtained in Example 19.
Figure 5:
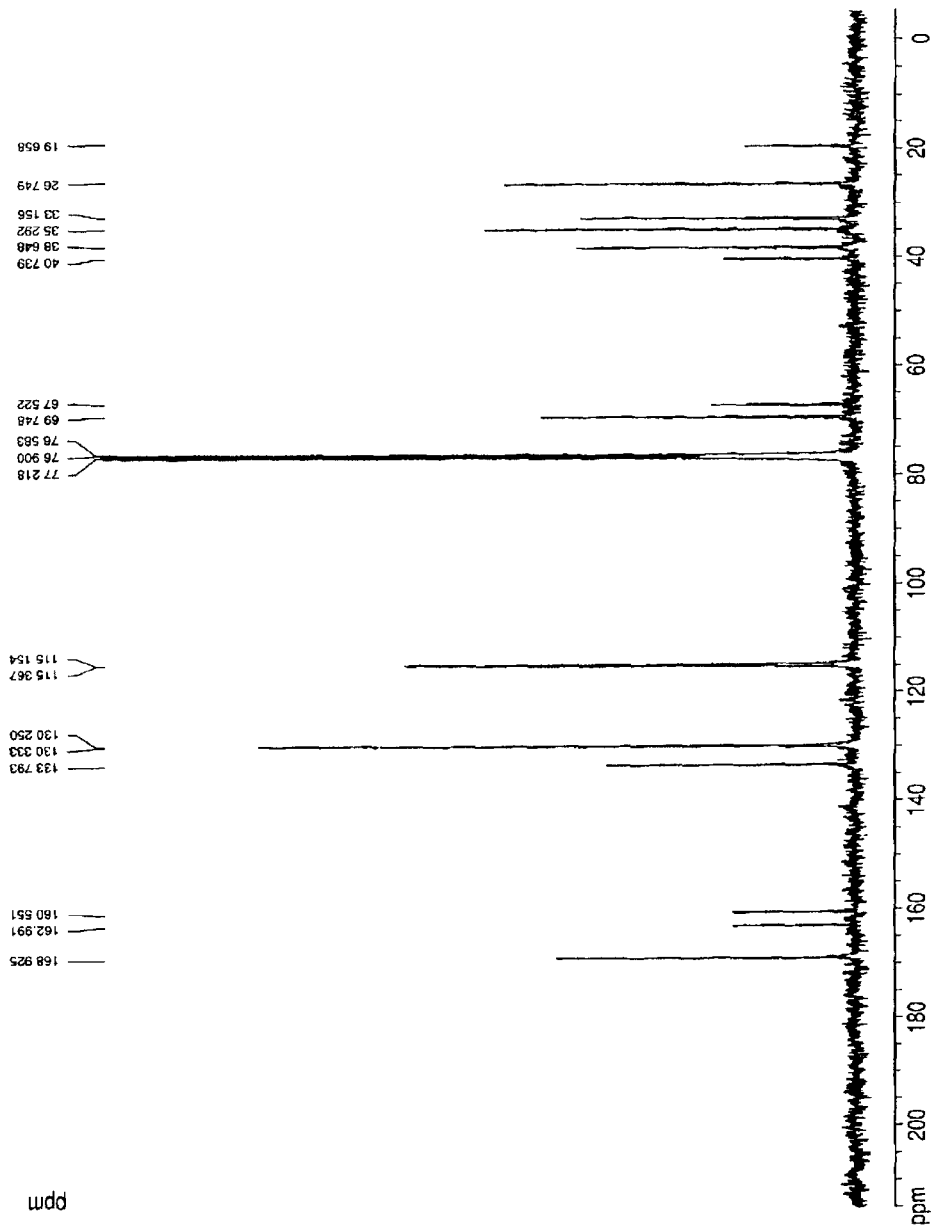
FIG. 5 shows the $^{13}C$ NMR spectrum of the PHA obtained in the Example 19.

FIG. 4 shows measured $^1$H-NMR spectra. Identification results thereof are given in Table 7 below. FIG. 5 shows measured $^{13}$C-NMR spectra. Identification results thereof are given in Table 8 below.

TABLE 7

| Chemical shifts (ppm) | Integration | Splitting patterns | Identification |
|---|---|---|---|
| 1.83 | 2 H | qurt | d1 |
| 2.35–2.58 | 4 H | m | b1, e1 |
| 3.64 | 2 H | s | f1 |
| 5.20 | 1 H | m | c1 |
| 6.92–6.98 | 2 H | m | j1, k1 |
| 7.23–7.26 | 2 H | m | h1, l1 |

TABLE 8

| Chemical shifts (ppm) | Identification |
| --- | --- |
| 26.7 | d1 |
| 33.2 | e1 |
| 35.3 | f1 |
| 38.6 | b1 |
| 69.7 | c1 |
| 115.1 & 115.4 | i1, k1 |
| 130.3 & 130.3 | h1, l1 |
| 133.7 | g1 |
| 160.6 & 163.0 | j1 |
| 168.9 | a1 |

From the results shown in the Tables 7 and 8, the PHA comprises a monomer unit of 3-hydroxy-5-{[(4-fluorophenyl)methyl]sulfanyl}valerate, and other monomer units of 3-hydroxyalkanoates and/or 3-hydroxyalkenoates having 4 to 12 carbon atoms such as 3-hydroxybutyric acid and 3-hydroxyvaleric acid. More specifically, the PHA has a structure represented by the following chemical formula (19):

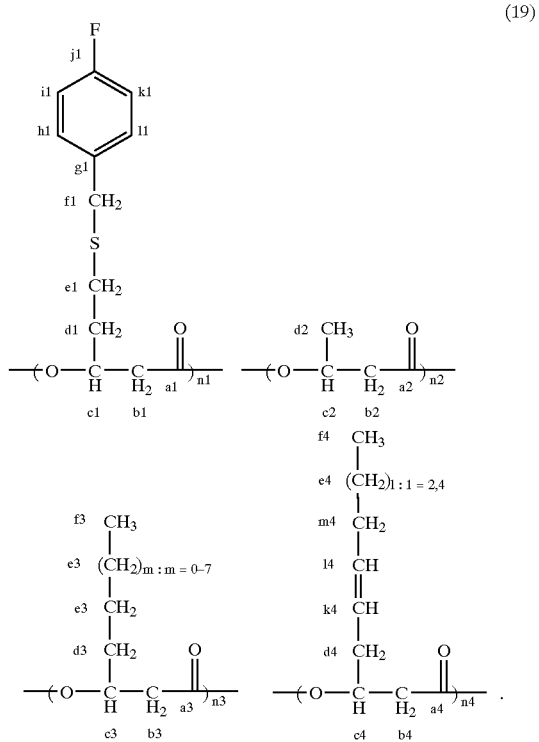

The integration of the $^1$H-NMR spectra indicated that the resulting PHA contains 76.7 mol % of 3-hydroxy-5-{[(4-fluorophenyl)methyl]sulfanyl}valerate monomer unit.

Example 20

*Pseudomonas cichorii* YN2 was inoculated to 200 mL of M9 medium that contains 0.1% of nonanoic acid and 0.1% of 5-{[(4-fluorophenyl)methyl]sulfanyl}valeric acid and cultured with shaking at 125 strokes/min at 30° C. for 48 hours. Then, the cells were collected by centrifugation, washed once with cold methanol, and lyophilized. The weight of the lyophilized cells was weighed (dry weight of the cells).

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 89 mg of polyhydroxyalkanoate.

The PHA obtained was subjected to NMR analysis and average molecular weight determination under the conditions as in Example 19. From the results of the NMR analysis, it was revealed that the PHA in this example comprises a monomer unit of 3-hydroxy-5-{[(4-fluorophenyl)methyl]sulfanyl}valerate and other monomer units of 3-hydroxyalkanoates and/or 3-hydroxyalkenoates having 4 to 12 carbon atoms such as 3-hydroxybutyrate and 3-hydroxyvalerate to confirm that it has a constitution represented by the chemical formula (19). The integration of the $^1$H-NMR spectra indicated that the PHA of this example contains 27.0 mol % of 3-hydroxy-5-{[(4-fluorophenyl)methyl]sulfanyl}valerate monomer unit.

Example 21

*Pseudomonas cichorii* YN2 was inoculated to 200 mL of M9 medium containing 0.5% of yeast extract (DIFCO) and 0.1% of 5-{[(4-fluorophenyl)methyl]sulfanyl}valeric acid, and cultured with shaking at 125 strokes/min at 30° C. for 48 hours. Then, the cells were collected by centrifugation, washed once with cold methanol, and lyophilized. The weight of the lyophilized cells was weighed (dry weight of the cells).

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 69 mg of polyhydroxyalkanoate in this Example.

The PHA obtained was subjected to NMR analysis and average molecular weight determination under the conditions as set forth in the Example 19. From the results of the NMR analysis, it was revealed that the PHA in this example comprises a monomer unit of 3-hydroxy-5-{[(4-fluorophenyl)methyl]sulfanyl}valerate and other monomer units of 3-hydroxyalkanoates and/or 3-hydroxyalkenoates having 4 to 12 carbon atoms such as 3-hydroxybutyrate and 3-hydroxyvalerate to confirm that it has a constitution represented by the above chemical formula (19). The integration of the $^1$H-NMR spectra indicated that the PHA of this example contains 76.7 mol % of 3-hydroxy-5-{[(4-fluorophenyl)methyl]sulfanyl}valerate monomer unit.

Example 22

*Pseudomonas cichorii* YN2 was inoculated to 200 mL of M9 medium containing 0.5% of sodium glutamate and 0.1% of 5-{[(4-fluorophenyl)methyl]sulfanyl}valeric acid, and cultured with shaking at 125 strokes/min at 30° C. for 48 hours. Then, the cells were collected by centrifugation, washed once with cold methanol, and lyophilized. The weight of the lyophilized cells was weighed (dry weight of the cells).

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield. 68 mg of polyhydroxyalkanoate in this Example.

The PHA obtained was subjected to NMR analysis and average molecular weight determination under the same conditions as set forth in Example 19. From the results of the NMR analysis, it was revealed that the PHA in this example comprises a monomer unit of 3-hydroxy-5-{[(4-fluorophenyl)methyl]sulfanyl}valerate and other monomer units of 3-hydroxyalkanoates and/or 3-hydroxyalkenoates having 4 to 12 carbon atoms, such as 3-hydroxybutyrate and 3-hydroxyvalerate, confirming that it has a constitution represented by the chemical formula (19). The integration of the $^3$H-NMR spectra indicated that the PHA of this example contains 90.3 mol % of 3-hydroxy-5-{[(4-fluorophenyl)methyl]sulfanyl}valerate monomer unit.

Example 23

*Pseudomonas cichorii* YN2 was inoculated to 200 mL of M9 medium containing 0.5% of D-glucose and 0.1% of 5-{[(4-fluorophenyl)methyl]sulfanyl}valeric acid, and cultured with shaking at 125 strokes/min at 30° C. for 48 hours. Then, the cells were collected by centrifugation, re-suspended in 200 mL of M9 medium containing 0.5% of D-glucose and 0.1% of 5-([(4-fluorophenyl)methyl]sulfanyl}valeric acid but no nitrogen source ($NH_4Cl$), and cultured at 30° C. with shaking at 125 strokes/min for 48 hours. After that, the cells were collected by centrifugation, washed once with cold methanol, and lyophilized. The weight of the lyophilized cells was weighed (dry weight of the cells).

The lyophilized pellet was suspended in 20 mL of chloroform and stirred at 60° C. for 20 hours to extract polyhydroxyalkanoate. The extract was filtered through a membrane filter of a pore size of 0.45 µm and concentrated by a rotary evaporator. The concentrated solution was precipitated with cold methanol. The precipitate was recovered and dried in vacuum to yield 164 mg of polyhydroxyalkanoate.

The PHA obtained was subjected to NMR analysis, and the average molecular weight determination under the conditions as set forth in Example 19. The results of the NMR analysis show that the PHA in this example comprises a monomer unit of 3-hydroxy-5-{[(4-fluorophenyl)methyl]sulfanyl}valerate and other monomer units of 3-hydroxyalkanoates and/or 3-hydroxyalkenoates having 4 to 12 carbon atoms, such as 3-hydroxybutyrate and 3-hydroxyvalerate to confirm that it has a constitution represented by the chemical formula (19). The integration of the $^1$H-NMR spectra indicated that the PHA of this example contains 85.9 mol % of 3-hydroxy-5-{[(4-fluorophenyl)methyl]sulfanyl}valerate monomer unit.

Example 24

*Pseudomonas cichorii* H45 was inoculated to 200 mL of M9 medium containing 0.5% of D-glucose and 0.1% of 5-{[(4-fluorophenyl)methyl]sulfanyl}valeric acid and cultured with shaking at 125 strokes/min at 30° C. for 48 hours. Then, the cells were collected by centrifugation, re-suspended in 200 mL of M9 medium containing 0.5% of D-glucose and 0.1% of 5-{[(4-fluorophenyl)methyl]sulfanyl}valeric acid but no nitrogen source ($NH_4Cl$), and cultured at 30° C. with shaking at 125 strokes/min for 48 hours. After that, the cells were collected by centrifugation, washed once with cold methanol, and lyophilized. The weight of the lyophilized cells was weighed (dry weight of the cells).

The lyophilized pellet was suspended in 20 mL of chloroform and stirred at 60° C. for 20 hours to extract polyhydroxyalkanoate. The extract was filtered through a membrane filter of a pore size of 0.45 µm and concentrated by a rotary evaporator. The concentrated solution was precipitated with cold methanol. The precipitate was recovered and dried in vacuum to yield 138 mg of polyhydroxyalkanoate.

The PHA obtained was subjected to NMR analysis, and the average molecular weight determination under the conditions as set forth in Example 19. The results of the NMR analysis show that the PHA in this example comprises a monomer unit of 3-hydroxy-5-{[(4-fluorophenyl)methyl]sulfanyl}valerate and other monomer units of 3-hydroxyalkanoates and/or 3-hydroxyalkenoates having 4 to 12 carbon atoms, such as 3-hydroxybutyrate and 3-hydroxyvalerate to confirm that it has a constitution represented by the chemical formula (19). The integration of the $^1$H-NMR spectra indicated that the PHA of this example contains 90.7 mol % of 3-hydroxy-5-{[(4-fluorophenyl)methyl]sulfanyl}valerate monomer unit.

Example 25

*Pseudomonas jessenii* P161 was inoculated to 200 mL of M9 medium containing 0.5% of D-glucose and 0.1% of 5-{[(4-fluorophenyl)methyl]sulfanyl}valeric acid, and cultured with shaking at 125 strokes/min at 30° C. for 48 hours. Then, the cells were collected by centrifugation, re-suspended in 200 mL of M9 medium containing 0.5% of D-glucose and 0.1% of 5-{[(4-fluorophenyl)methyl]sulfanyl}valeric acid but no nitrogen source ($NH_4Cl$), and cultured at 30° C. with shaking at 125 strokes/min for 48 hours. After that, the cells were collected by centrifugation, washed once with cold methanol, and lyophilized. The weight of the lyophilized cells was weighed (the cell dry weight).

The lyophilized pellet was suspended in 20 mL of chloroform and stirred at 60° C. for 20 hours to extract polyhydroxyalkanoate. The extract was filtered through a membrane filter of a pore size of 0.45 µm and concentrated by a rotary evaporator. The concentrated solution was precipitated with cold methanol. The precipitate was recovered and dried in vacuum to yield 138 mg of polyhydroxyalkanoate.

The PHA obtained was subjected to NMR analysis, and the average molecular weight determination under the conditions as set forth in Example 19. The results of the NMR analysis show that the PHA in this example comprises a monomer unit of 3-hydroxy-5-{[(4-fluorophenyl)methyl]sulfanyl}valerate and other monomer units of 3-hydroxyalkanoates and/or 3-hydroxyalkenoates having 4 to 12 carbon atoms, such as 3-hydroxybutyrate or 3-hydroxyvalerate to confirm that it has a constitution represented by the chemical formula (19). The integration of the $^1$H-NMR spectra indicated that the PHA of this example contains 88.5 mol % of 3-hydroxy-5-{[(4-fluorophenyl)methyl]sulfanyl}valerate monomer unit.

Example 26

*Pseudomonas cichorii* YN2 was inoculated to 200 mL of M9 medium containing 0.5% of polypeptone (Wako Pure Chemical Industries, Ltd.) and 0.1% of 5-{[(4-fluorophenyl)methyl]sulfanyl}valeric acid and cultured with shaking at 125 strokes/min at 30° C. for 48 hours. Then, the cells were collected by centrifugation, re-suspended in 200 mL of M9 medium containing 0.5% of sodium pyruvate and 0.1% of 5-{[(4-fluorophenyl)methyl]sulfanyl}valeric acid but no nitrogen source ($NH_4Cl$), and cultured at 30° C. with shaking at 125 strokes/min for 48 hours. After that, the cells were collected by centrifugation, washed once with cold methanol, and lyophilized. The weight of the lyophilized cells was weighed (the cell dry weight).

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 125 mg of polyhydroxyalkanoate.

The PHA obtained was subjected to NMR analysis, and the average molecular weight determination under the conditions as set forth in Example 19. The results of the NMR analysis show that the PHA in this example comprises a monomer unit of 3-hydroxy-5-{[(4-fluorophenyl)methyl]sulfanyl}valerate and other monomer units of 3-hydroxyalkanoates and/or 3-hydroxyalkenoates having 4 to 12 carbon atoms, such as 3-hydroxybutyrate or 3-hydroxyvalerate to confirm that it has a constitution represented by the chemical formula (19). The integration of the $^1$H-NMR spectra indicated that the PHA of this example contains 89.5 mol % of 3-hydroxy-5-{[(4-fluorophenyl)methyl]sulfanyl}valerate monomer unit.

Example 27

*Pseudomonas cichorii* H45 was inoculated to 200 mL of M9 medium containing 0.5% of polypeptone (Wako Pure Chemical Industries, Ltd.) and 0.1% of 5-{[(4-fluorophenyl)methyl]sulfanyl}valeric acid and cultured with shaking at 125 strokes/min at 30° C. for 48 hours. Then, the cells were collected by centrifugation, re-suspended in 200 mL of M9 medium containing 0.5% of sodium pyruvate and 0.1% of 5-{[(4-fluorophenyl)methyl]sulfanyl}valeric acid but no nitrogen source ($NH_4Cl$), and cultured at 30° C. with shaking at 125 strokes/min for 48 hours. After that, the cells were collected by centrifugation, washed once with cold methanol, and lyophilized. The weight of the lyophilized cells was weighed (the cell dry weight).

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 154 mg of polyhydroxyalkanoate.

The PHA obtained was subjected to NMR analysis, and the average molecular weight determination under the conditions as set forth in Example 19. The results of the NMR analysis show that the PHA in this example comprises a monomer unit of 3-hydroxy-5-{[(4-fluorophenyl)methyl]sulfanyl}valerate and other monomer units of 3-hydroxyalkanoates and/or 3-hydroxyalkenoates having 4 to 12 carbon atoms, such as 3-hydroxybutyrate or 3-hydroxyvalerate to confirm that it has a constitution represented by the chemical formula (19). The integration of the $^1$H-NMR spectra indicated that the PHA of this example contains 97.9 mol % of 3-hydroxy-5-{[(4-fluorophenyl)methyl]sulfanyl}valerate monomer unit.

Example 28

*Pseudomonas jessenii* P161 was inoculated to 200 mL of M9 medium containing 0.5% of polypeptone (Wako Pure Chemical Industries, Ltd.) and 0.1% of 5-{[(4-fluorophenyl)methyl]sulfanyl}valeric acid and cultured with shaking at 125 strokes/min at 30° C. for 48 hours. Then, the cells were collected by centrifugation, re-suspended in 200 mL of M9 medium containing 0.5% of sodium pyruvate and 0.1% of 5-{[(4-fluorophenyl)methyl]sulfanyl}valeric acid but no nitrogen source ($NH_4Cl$), and cultured at 30° C. with shaking at 125 strokes/min for 48 hours. After that, the cells were collected by centrifugation, washed once with cold methanol, and lyophilized. The weight of the lyophilized cells was weighed (the cell dry weight).

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 158 mg of polyhydroxyalkanoate.

The PHA obtained was subjected to NMR analysis, and the average molecular weight determination under the conditions as set forth in Example 19. The results of the NMR analysis show that the PHA in this example comprises a monomer unit of 3-hydroxy-5-{[(4-fluorophenyl)methyl]sulfanyl}valerate and other monomer units of 3-hydroxyalkanoates and/or 3-hydroxyalkenoates having 4 to 12 carbon atoms, such as 3-hydroxybutyrate or 3-hydroxyvalerate to confirm that it has a constitution represented by the chemical formula (19). The integration of the $^1$H-NMR spectra indicated that the PHA of this example contains 91.6 mol % of 3-hydroxy-5-{[(4-fluorophenyl)methyl]sulfanyl}valerate monomer unit.

Table 9 shows the dry weight of the cells, the dry weight of the polymer, the dry weight ratio of the polymer to the cells, and the amount in mol % of the 3-hydroxy-5-{[(4-fluorophenyl)methyl]sulfanyl}valerate unit (abbreviated as "3HFBzyTV") in the resulting PHA polymer in Examples 19 to 28.

TABLE 9

|  | Cell Dry Weight (mg/L) | Polymer Dry Weight (mg/L) | Polymer Weight/ Cell Weight (%) | 3HFBzyTV Unit mol % |
|---|---|---|---|---|
| Example 19 | 945 | 530 | 56.1 | 76.7 |
| Example 20 | 680 | 445 | 65.4 | 27.0 |
| Example 21 | 915 | 345 | 37.7 | 76.7 |
| Example 22 | 740 | 340 | 45.9 | 90.3 |
| Example 23 | 1120 | 820 | 73.2 | 85.9 |
| Example 24 | 940 | 690 | 73.4 | 90.7 |
| Example 25 | 955 | 690 | 72.3 | 88.5 |
| Example 26 | 1015 | 625 | 61.6 | 89.5 |
| Example 27 | 1125 | 770 | 68.4 | 97.9 |
| Example 28 | 1215 | 790 | 65.0 | 91.6 |

Process for Producing Polyhydroxyalkanoate Comprising 3-Hydroxy-4-{[(4-Fluorophenyl)Methyl]Sulfanyl}Butyric Acid Monomer Unit Example 29

*Pseudomonas cichorii* YN2 was inoculated to 200 mL of M9 medium containing 0.5% of yeast extract (DIFCO) and 0.1% of 4-{[(4-fluorophenyl)methyl]sulfanyl}butyric acid, and cultured with shaking at 125 strokes/min at 30° C. for 48 hours. Then, the cells were collected by centrifugation, washed once with cold methanol, and lyophilized. The weight of the lyophilized cells was weighed (dry weight of the cells).

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 41 mg of polyhydroxyalkanoate.

The average molecular weight of the resulting PHA was determined by gel permeation chromatography (GPC; TOSOH HLC-8220, column; TOSOH TSK-GEL SuperHM-H, solvent; chloroform, polystyrene equivalent). As a result, the number average molecular weight Mn was 15,300 and the weight average molecular weight Mw was 37,100.

In order to identify the structure of the PHA obtained, the PRA was subjected to NMR analysis under the following conditions.

Figure 6:
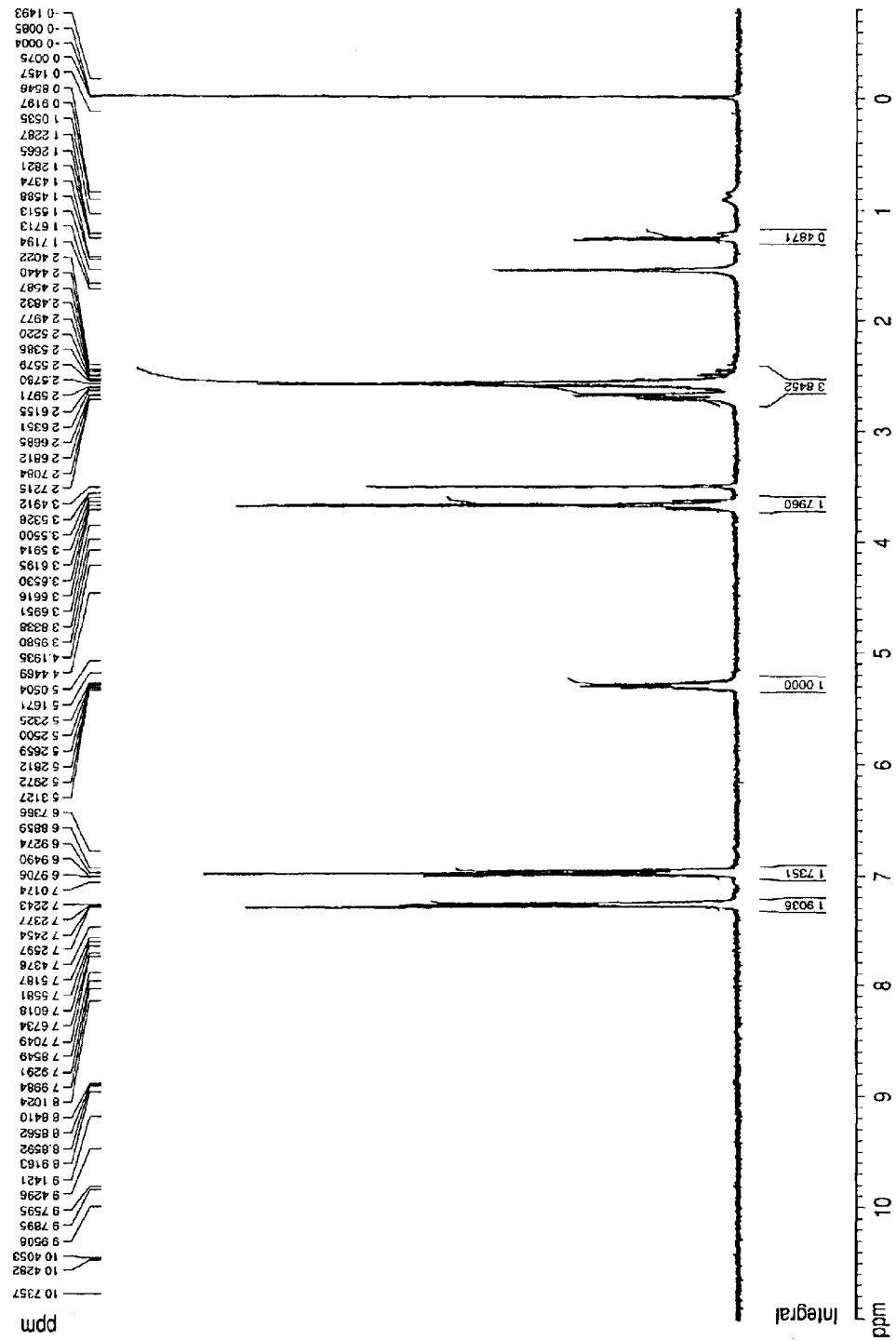
FIG. 6 shows the $^1H$ NMR spectrum of a PHA obtained in Example 29.

Spectrometer
  FT-NMR: Bruker DPX 400 with spectrometer frequencies of 400 MHz for $^1$H-NMR.
Conditions
  Nuclear Species: $^1$H
  Solvent: $CDCl_3$
  Reference: $TMS/CDCl_3$ in capillary
  Temperature: room temperature FIG. 6 shows measured $^1$H-NMR spectra. Identification results thereof are given in Table 10 below.

TABLE 10

| Chemical shifts (ppm) | Integration | Splitting patterns | Identification |
|---|---|---|---|
| 2.40–2.72 | 4 H | m | b1, d1 |
| 3.65 | 2 H | m | e1 |
| 5.27 | 1 H | m | c1 |
| 6.95 | 2 H | m | h1, j1 |
| 7.23 | 2 H | m | g1, k1 |

From the results shown in the Table 10, the subject PHA comprises a monomer unit of 3-hydroxy-4-{[(4-fluorophenyl)methyl]sulfanyl}butyrate and other monomer units of 3-hydroxyalkanoates and/or 3-hydroxyalkenoates having 4 to 12 carbon atoms, such as 3-hydroxybutyrate or 3-hydroxyvalerate. More specifically, the PHA has a structure represented by the following chemical formula (20).

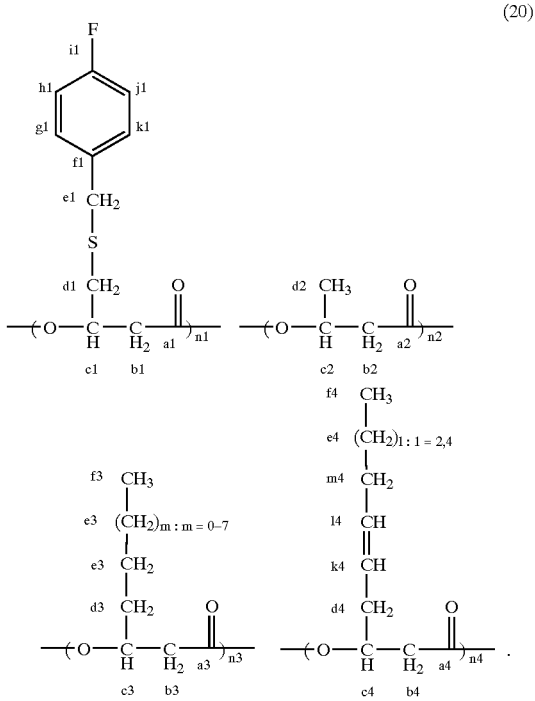

(20)

The integration of the $^1$H-NMR spectra indicated that the resulting PHA contains 89.8 mol % of 3-hydroxy-4-{(4-fluorophenyl)methyl]sulfanyl}butyrate monomer unit.

Example 30

*Pseudomonas cichorii* YN2 was inoculated to 200 mL of M9 medium containing 0.1% of nonanoic acid and 0.1% of 4-{[(4-fluorophenyl)methyl]sulfanyl}butyric acid and cultured with shaking at 125 strokes/min at 30° C. for 48 hours. Then the cells were collected by centrifugation, washed once with cold methanol, and lyophilized and weighed to determine dried cell weight.

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 45 mg of polyhydroxyalkanoate.

The PHA obtained was subjected to NMR analysis, and the average molecular weight determination under the conditions as set forth in Example 29. The results of the NMR analysis show that the PHA in this example comprises a monomer unit of 3-hydroxy-4-{[(4-fluorophenyl)methyl]sulfanyl}butyrate and other monomer units of 3-hydroxyalkanoates and/or 3-hydroxyalkenoates having 4 to 12 carbon atoms, such as 3-hydroxybutyrate or 3-hydroxyvalerate to confirm that it has a constitution represented by the chemical formula (20). The integration of the $^1$H-NMR spectra indicated that the PHA of this example contains 10.6 mol % of 3-hydroxy-4-{[(4-fluorophenyl)methyl]sulfanyl}butyrate monomer unit.

Example 31

*Pseudomonas cichorii* YN2 was inoculated to 200 mL of M9 medium containing 0.5% of sodium glutamate and 0.1% of 4-{[(4-fluorophenyl)methyl]sulfanyl}butyric acid and cultured with shaking at 125 strokes/min at 30° C. for 48 hours. Then, the cells were collected by centrifugation, washed once with cold methanol, lyophilized and weighed.

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 11 mg of polyhydroxyalkanoate.

The PHA obtained was subjected to NMR analysis, and the average molecular weight determination under the conditions as set forth in Example 29. The results of the NMR analysis show that the PHA in this example comprises a monomer unit of 3-hydroxy-4-{[(4-fluorophenyl)methyl]sulfanyl}butyrate and other monomer units of 3-hydroxyalkanoates and/or 3-hydroxyalkenoates having 4 to 12 carbon atoms, such as 3-hydroxybutyrate or 3-hydroxyvalerate to confirm that it has a constitution represented by the chemical formula (20). The integration of the $^1$H-NMR spectra indicated that the PHA of this example contains 84.1 mol % of 3-hydroxy-4-{[(4-fluorophenyl)methyl]sulfanyl}butyrate monomer unit.

Example 32

*Pseudomonas cichorii* YN2 was inoculated to 200 mL of M9 medium containing 0.5% of D-glucose and 0.1% of 4-{[(4-fluorophenyl)methyl]sulfanyl}butyric acid and cultured with shaking at 125 strokes/min at 30° C. for 48 hours. Then, the cells were collected by centrifugation, re-suspended in 200 mL of M9 medium containing 0.5% of D-glucose and 0.1% of 4-{[[4-fluoromethyl]phenyl]

methyl}sulfanyl]butyric acid but no nitrogen source (NH₄Cl), and cultured at 30° C. with shaking at 125 strokes/min for 48 hours. After that, the cells were collected by centrifugation, washed once with cold methanol, lyophilized and weighed as the dry cell weight.

The lyophilized pellet was suspended in 20 mL of chloroform and stirred at 60° C. for 20 hours to extract polyhydroxyalkanoate. The extract was filtered through a membrane filter of a pore size of 0.45 µm and concentrated by a rotary evaporator. The concentrated solution was precipitated with cold methanol. The precipitate was recovered and dried in vacuum to yield 153 mg of polyhydroxyalkanoate.

The PHA obtained was subjected to NMR analysis, and the average molecular weight determination under the conditions as set forth in Example 29. The results of the NMR analysis show that the PHA in this example comprises a monomer unit of 3-hydroxy-4-{[(4-fluorophenyl)methyl]sulfanyl}butyrate and other monomer units of 3-hydroxyalkanoates and/or 3-hydroxyalkenoates having 4 to 12 carbon atoms, such as 3-hydroxybutyrate or 3-hydroxyvalerate to confirm that it has a constitution represented by the chemical formula (20). The integration of the ¹H-NMR spectra indicated that the PHA of this example contains 68.5 mol % of 3-hydroxy-4-{[(4-fluorophenyl)methyl]sulfanyl}butyrate monomer unit.

Example 33

*Pseudomonas cichorii* H45 was inoculated to 200 mL of M9 medium containing 0.5% of polypeptone (Wako Pure Chemical Industries, Ltd.) and 0.1% of 4-{[(4-fluorophenyl)methyl]sulfanyl}butyric acid, and cultured with shaking at 125 strokes/min at 30° C. for 48 hours. Then, the cells were collected by centrifugation, re-suspended in 200 mL of M9 medium containing 0.5% of sodium pyruvate and 0.1% of 4-{[(4-fluorophenyl)methyl]sulfanyl}butyric acid but no nitrogen source (NH₄Cl), and cultured at 30° C. with shaking at 125 strokes/min for 48 hours. After that, the cells were collected by centrifugation, washed once with cold methanol, and lyophilized. The weight of the lyophilized cells was weighed (the cell dry weight).

The lyophilized pellet was suspended in 20 mL of chloroform and stirred at 60° C. for 20 hours to extract polyhydroxyalkanoate. The extract was filtered through a membrane filter of a pore size of 0.45 µm and concentrated by a rotary evaporator. The concentrated solution was precipitated with cold methanol. The precipitate was recovered and dried in vacuum to yield 38 mg of polyhydroxyalkanoate.

The PHA obtained was subjected to NMR analysis, and the average molecular weight determination under the conditions as set forth in Example 29. The results of the NMR analysis show that the PHA in this example comprises a monomer unit of 3-hydroxy-4-{[(4-fluorophenyl)methyl]sulfanyl}butyrate and other monomer units of 3-hydroxyalkanoates and/or 3-hydroxyalkenoates having 4 to 12 carbon atoms, such as 3-hydroxybutyrate or 3-hydroxyvalerate to confirm that it has a constitution represented by the chemical formula (20). The integration of the ¹H-NMR spectra indicated that the PHA of this example contains 43.1 mol % of 3-hydroxy-4-{[(4-fluorophenyl)methyl]sulfanyl}butyrate monomer unit.

Example 34

*Pseudomonas jessenii* P161 was inoculated to 200 mL of M9 medium containing 0.5% of D-glucose and 0.1% of 4-{[(4-fluorophenyl)methyl]sulfanyl}butyric acid, and cultured with shaking at 125 strokes/min at 30° C. for 48 hours. Then, the cells were collected by centrifugation, re-suspended in 200 mL of M9 medium containing 0.5% of D-glucose and 0.1% of 4-{[(4-fluorophenyl)methyl]sulfanyl}butyric acid but no nitrogen source (NH₄Cl), and cultured at 30° C. with shaking at 125 strokes/min for 48 hours. After that, the cells were collected by centrifugation, washed once with cold methanol, and lyophilized. The weight of the lyophilized cells was weighed (the cell dry weight).

The lyophilized pellet was suspended in 20 mL of chloroform and stirred at 60° C. for 20 hours to extract polyhydroxyalkanoate. The extract was filtered through a membrane filter of a pore size of 0.45 µm and concentrated by a rotary evaporator. The concentrated solution was precipitated with cold methanol. The precipitate was recovered and dried in vacuum to yield 47 mg of polyhydroxyalkanoate.

The PHA obtained was subjected to NMR analysis, and the average molecular weight determination under the conditions as set forth in Example 29. The results of the NMR analysis show that the PHA in this example comprises a monomer unit of 3-hydroxy-4-{[(4-fluorophenyl)methyl]sulfanyl}butyrate and other monomer units of 3-hydroxyalkanoates and/or 3-hydroxyalkenoates having 4 to 12 carbon atoms, such as 3-hydroxybutyrate or 3-hydroxyvalerate to confirm that it has a constitution represented by the chemical formula (20). The integration of the ¹H-NMR spectra indicated that the PHA of this example contains 48.7 mol % of 3-hydroxy-4-{[(4-fluorophenyl)methyl]sulfanyl}butyrate monomer unit.

Table 11 shows the dry weight of the cells, the dry weight of the polymer, the dry weight ratio of the polymer to the cells, and the amount in mol % of 3-hydroxy-4-{[(4-fluorophenyl)methyl]sulfanyl}butyrate unit (abbreviated as "3HFBzyTB") in the resulting PHA polymer in Examples 29 to 34.

TABLE 11

| | Cell Dry Weight (mg/L) | Polymer Dry Weight (mg/L) | Polymer Weight/ Cell Weight (%) | 3HFBzyTB Unit mol % |
|---|---|---|---|---|
| Example 29 | 975 | 205 | 21.0 | 89.8 |
| Example 30 | 515 | 225 | 43.7 | 10.6 |
| Example 31 | 955 | 55 | 5.8 | 84.1 |
| Example 32 | 1365 | 765 | 56.0 | 68.5 |
| Example 33 | 515 | 190 | 30.1 | 43.1 |
| Example 34 | 780 | 235 | 36.9 | 48.7 |

What is claimed is:

1. A polyhydroxyalkanoate comprising a unit represented by the following chemical formula (1):

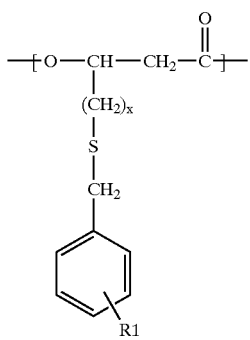

(1)

x = 1–8 wherein R1 is a substituent of an aromatic ring selected from the group consisting of H, $CH_3$, $C_2H_5$, $CH_3CH_2CH_2$, $(CH_3)_2CH$, $(CH_3)_3C$, a halogen atom, CN, $NO_2$, COOR', and $SO_2R''$, wherein R' is selected from the group consisting of H, Na, K, $CH_3$, and $C_2H_5$, and R" is selected from the group consisting of OH, a halogen atom, ONa, OK, $OCH_3$, and $OC_2H_5$; and x represents an integer of 1 to 8 being the same or different each other in the polyhydroxyalkanoate, with the proviso that the polyhydroxyalkanoate does not consist of two units represented by the following chemical formulae (2) and (3):

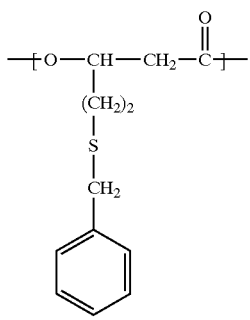

(2)

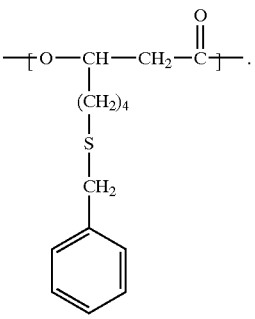

(3)

2. The polyhydroxyalkanoate according to claim 1, wherein the polyhydroxyalkanoate further comprises one or more units selected from the group consisting of units represented by the following chemical formulae (4) and (5):

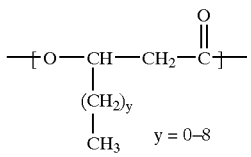

(4)

y = 0–8

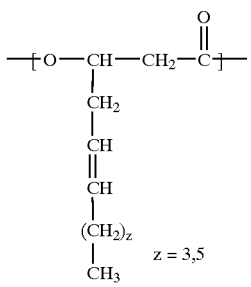

(5)

z = 3,5 wherein y is an integer of 0–8, and z is an integer of 3 or 5.

3. The polyhydroxyalkanoate according to claim 1, wherein the polyhydroxyalkanoate comprises a unit of 3-hydroxy-5-[(phenylmethyl)sulfanyl]valerate represented by the following chemical formula (2):

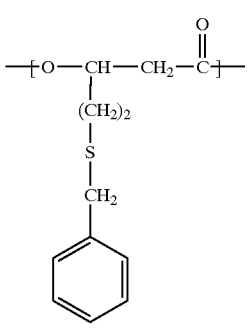

(2)

4. The polyhydroxyalkanoate according to claim 1, wherein the polyhydroxyalkanoate comprises a unit of 3-hydroxy-4-[(phenylmethyl)sulfanyl]butyrate represented by the following chemical formula (6):

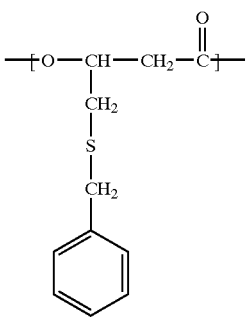

(6)

5. The polyhydroxyalkanoate according to claim 1, the polyhydroxyalkanoate comprises a unit of 3-hydroxy-5-{[(4-methylphenyl)methyl]sulfanyl}valerate represented by the following chemical formula (7):

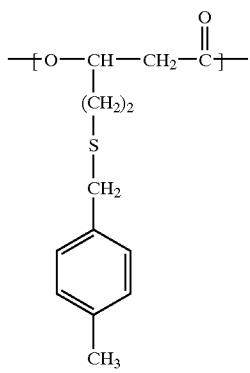

(7)

6. The polyhydroxyalkanoate according to claim 1, wherein the polyhydroxyalkanoate comprises a unit of 3-hydroxy-5-{[(4-fluorophenyl)methyl]sulfanyl}valerate represented by the following general formula (8):

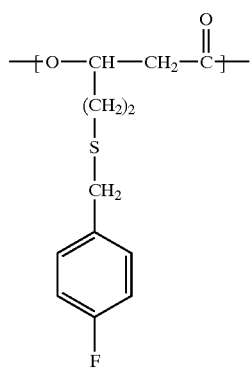

(8)

7. The polyhydroxyalkanoate according to claim 1, wherein the polyhydroxyalkanoate comprises a unit of 3-hydroxy-4-{[(4-fluorophenyl)methyl]sulfanyl}butyrate represented by the following chemical formula (9):

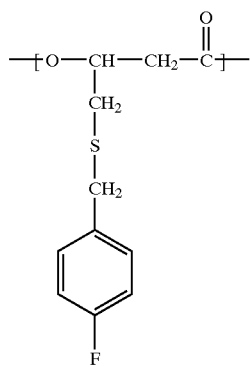

(9)

8. The polyhydroxyalkanoate according to claim 1, wherein the polyhydroxyalkanoate has a number average molecular weight within a range of 5,000 to 300,000.

9. A process for producing a polyhydroxyalkanoate that comprises a unit represented by the following chemical formula (1):

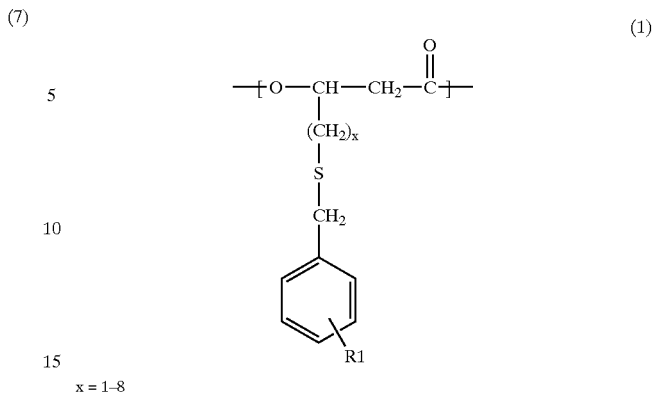

(1)

x = 1–8 wherein R1 is a substituent of an aromatic ring selected from the group consisting of H, $CH_3$, $C_2H_5$, $CH_3CH_2CH_2$, $(CH_3)_2CH$, $(CH_3)_3C$, a halogen atom, CN, $NO_2$, COOR', and $SO_2R''$, wherein R' is selected from the group consisting of H, Na, K, $CH_3$, and $C_2H_5$, and R'' is selected from the group consisting of OH, a halogen atom, ONa, OK, $OCH_3$, and $OC_2H_5$; and x represents an integer of 1 to 8 being the same or different each other in the polyhydroxyalkanoate, comprising the step of:
cultivating a microorganism in a culture medium containing a compound represented by the following chemical formula (10):

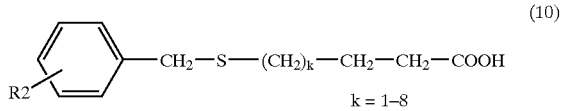

(10)

k = 1–8 wherein R2 is a substituent of an aromatic ring and selected the group consisting of H, $CH_3$, $C_2H_5$, $CH_3CH_2CH_2$, $(CH_3)_2CH$, $(CH_3)_3C$, a halogen atom, CN, $NO_2$, COOR' and $SO_2R''$, wherein R' is selected from the group consisting of H, Na, K, $CH_3$, and $C_2H_5$, and R'' is selected from the group consisting of OH, a halogen atom, ONa, OK, $OCH_3$, and $OC_2Hs$; and k represents an integer of 1 to 8.

10. The process according to claim 9, wherein the polyhydroxyalkanoate further comprises one or more units selected from the group consisting of units represented by the following chemical formulae (4) and (5):

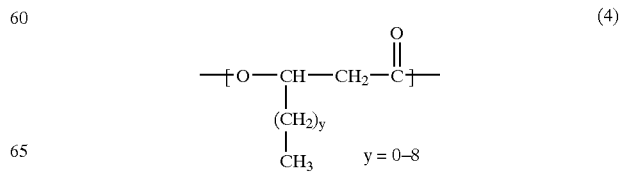

(4)

y = 0–8

(5)

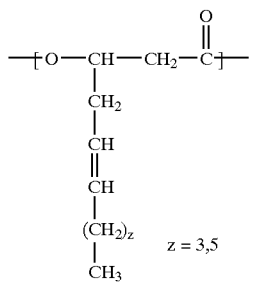

wherein y is an integer of 0–8, and z is an integer of 3 or 5.

11. A process for producing a polyhydroxyalkanoate that comprises a unit represented by the following chemical formula (1):

(1)

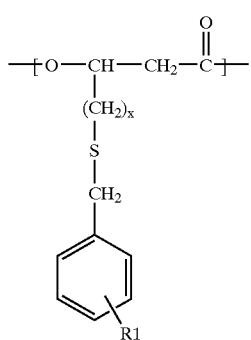

x = 1–8 wherein R1 is a substituent of an aromatic ring selected from the group consisting of H, $CH_3$, $C_2H_5$, $CH_3CH_2CH_2$, $(CH_3)_2CH$, $(CH_3)_3C$, a halogen atom, CN, $NO_2$, COOR', and $SO_2R''$, wherein R' is selected from the group consisting of H, Na, K, $CH_3$, and $C_2H_5$, and R'' is selected from the group consisting of OH, a halogen atom, ONa, OK, $OCH_3$, and $OC_2H_5$; and x represents an integer of 1 to 8 being the same or different each other in the polyhydroxyalkanoate, comprising the step of:
cultivating a microorganism in a culture medium containing a compound represented by the following chemical formula (10):

(10)

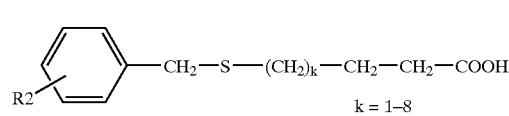

k = 1–8 wherein R2 is a substituent of an aromatic ring and selected the group consisting of H, $CH_3$, $C_2H_5$, $CH_3CH_2CH_2$, $(CH_3)_2CH$, $(CH_3)_3C$, a halogen atom, CN, $NO_2$, COOR' and $SO_2R''$, wherein R' is selected from the group consisting of H, Na, K, $CH_3$, and $C_2H_5$, and R'' is selected from the group consisting of OH, a halogen atom, ONa, OK, $OCH_3$, and $OC_2H_5$; and k represents an integer of 1 to 8, wherein the culture medium further contains polypeptone.

12. A process for producing a polyhydroxyalkanoate that comprises a unit represented by the following chemical formula (1):

(1)

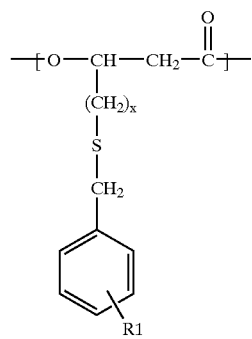

x = 1–8 wherein R1 is a substituent of an aromatic ring selected from the group consisting of H, $CH_3$, $C_2H_5$, $CH_3CH_2CH_2$, $(CH_3)_2CH$, $(CH_3)_3C$, a halogen atom, CN, $NO_2$, COOR', and $SO_2R''$, wherein R' is selected from the group consisting of H, Na, K, $CH_3$, and $C_2H_5$, and R'' is selected from the group consisting of OH, a halogen atom, ONa, OK, $OCH_3$, and $OC_2H_5$; and x represents an integer of 1 to 8 being the same or different each other in the polyhydroxyalkanoate, comprising the step of:
cultivating a microorganism in a culture medium containing a compound represented by the following chemical formula (10):

(10)

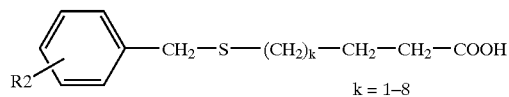

k = 1–8 wherein R2 is a substituent of an aromatic ring and selected the group consisting of H, $CH_3$, $C_2H_5$, $CH_3CH_2CH_2$, $(CH_3)_2CH$, $(CH_3)_3C$, a halogen atom, CN, $NO_2$, COOR' and $SO_2R''$, wherein R' is selected from the group consisting of H, Na, K, $CH_3$, and $C_2H_5$, and R'' is selected from the group consisting of OH, a halogen atom, ONa, OK, $OCH_3$, and $OC_2H_5$; and k represents an integer of 1 to 8, wherein the culture medium further contains yeast extract.

13. A process for producing a polyhydroxyalkanoate that comprises a unit represented by the following chemical formula (1):

(1)

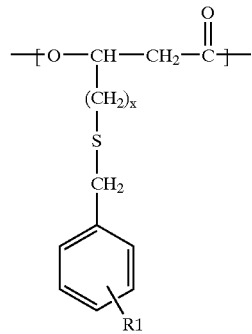

x = 1–8 wherein R1 is a substituent of an aromatic ring selected from the group consisting of H, $CH_3$, $C_2H_5$, $CH_3CH_2CH_2$, $(CH_3)_2CH$, $(CH_3)_3C$, a halogen atom, CN, $NO_2$, COOR', and $SO_2R''$, wherein R' is selected from the group consisting of H, Na, K, $CH_3$, and $C_2H_5$, and R'' is selected from the group consisting of OH, a halogen atom, ONa, OK, $OCH_3$, and $OC_2H_5$; and x represents an integer of 1 to 8 being the same or different each other in the polyhydroxyalkanoate, comprising the step of:
cultivating a microorganism in a culture medium containing a compound represented by the following chemical formula (10):

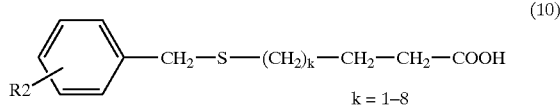

wherein R2 is a substituent of an aromatic ring and selected the group consisting of H, $CH_3$, $C_2H_5$, $CH_3CH_2CH_2$, $(CH_3)_2CH$, $(CH_3)_3C$, a halogen atom, CN, $NO_2$, COOR' and $SO_2R''$, wherein R' is selected from the group consisting of H, Na, K, $CH_3$, and $C_2H_5$, and R'' is selected from the group consisting of OH, a halogen atom, ONa, OK, $OCH_3$, and $OC_2H_5$; and k represents an integer of 1 to 8, wherein the culture medium further contains a saccharide.

14. The process according to claim 13, wherein the saccharide is one or more compounds selected from the group consisting of glyceraldehyde, erythrose, arabinose, xylose, glucose, galactose, mannose, fructose, glycerol, erythritol, xylitol, gluconic acid, glucuronic acid, galacturonic acid, maltose, sucrose, and lactose.

15. A process for producing a polyhydroxyalkanoate that comprises a unit represented by the following chemical formula (1):

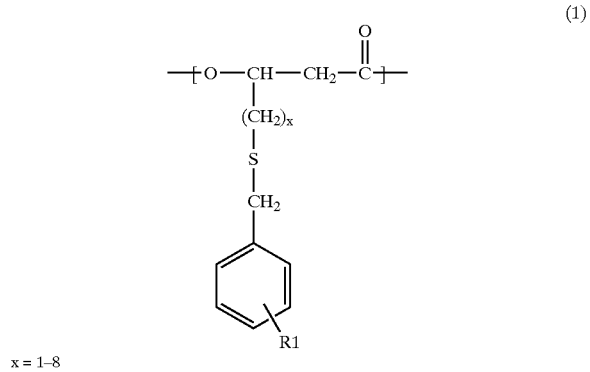

wherein R1 is a substituent of an aromatic ring selected from the group consisting of H, $CH_3$, $C_2H_5$, $CH_3CH_2CH_2$, $(CH_3)_2CH$, $(CH_3)_3C$, a halogen atom, CN, $NO_2$, COOR', and $SO_2R''$, wherein R' is selected from the group consisting of H, Na, K, $CH_3$, and $C_2H_5$, and R'' is selected from the group consisting of OH, a halogen atom, ONa, OK, $OCH_3$, and $OC_2H_5$; and x represents an integer of 1 to 8 being the same or different each other in the polyhydroxyalkanoate, comprising the step of:
cultivating a microorganism in a culture medium containing a compound represented by the following chemical formula (10):

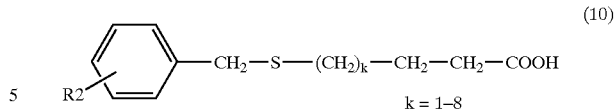

wherein R2 is a substituent of an aromatic ring and selected the group consisting of H, $CH_3$, $C_2H_5$, $CH_3CH_2CH_2$, $(CH_3)_2CH$, $(CH_3)_3C$, a halogen atom, CN, $NO_2$, COOR' and $SO_2R''$, wherein R' is selected from the group consisting of H, Na, K, $CH_3$, and $C_2H_5$, and R'' is selected from the group consisting of OH, a halogen atom, ONa, OK, $OCH_3$, and $OC_2H_5$; and k represents an integer of 1 to 8, wherein the culture medium further contains an organic acid or a salt thereof.

16. The process according to claim 15, wherein the organic acid or a salt thereof is one or more compounds selected from the group consisting of pyruvic acid, malic acid, lactic acid, citric acid, succinic acid and salts thereof.

17. A process for producing a polyhydroxyalkanoate that comprises a unit represented by the following chemical formula (1):

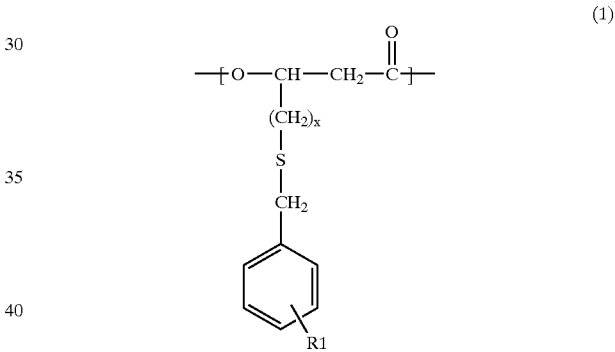

wherein R1 is a substituent of an aromatic ring selected from the group consisting of H, $CH_3$, $C_2H_5$, $CH_3CH_2CH_2$, $(CH_3)_2CH$, $(CH_3)_3C$, a halogen atom, CN, $NO_2$, COOR', and $SO_2R''$, wherein R' is selected from the group consisting of H, Na, K, $CH_3$, and $C_2H_5$, and R'' is selected from the group consisting of OH, a halogen atom, ONa, OK, $OCH_3$, and $OC_2H_5$; and x represents an integer of 1 to 8 being the same or different each other in the polyhydroxyalkanoate, comprising the step of:
cultivating a microorganism in a culture medium containing a compound represented by the following chemical formula (10):

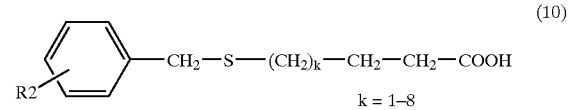

wherein R2 is a substituent of an aromatic ring and selected the group consisting of H, CH$_3$, C$_2$H$_5$, CH$_3$CH$_2$CH$_2$, (CH$_3$)$_2$CH, (CH$_3$)$_3$C, a halogen atom, CN, NO$_2$, COOR' and SO$_2$R", wherein R' is selected from the group consisting of H, Na, K, CH$_3$, and C$_2$H$_5$, and R" is selected from the group consisting of OH, a halogen atom, ONa, OK, OCH$_3$, and OC$_2$H$_5$; and k represents an integer of 1 to 8, wherein the culture medium further contains an amino acid or a salt thereof.

18. The process according to claim 17, wherein the amino acid or a salt thereof is one or more compounds selected from the group consisting of glutamic acid, aspartic acid, and salts thereof.

19. A process for producing a polyhydroxyalkanoate that comprises a unit represented by the following chemical formula (1):

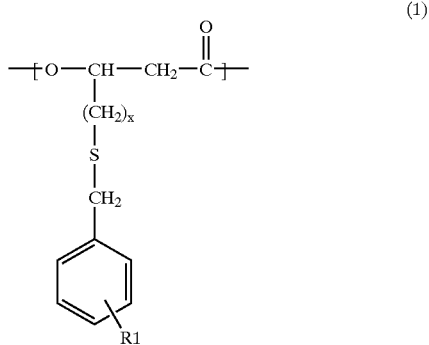

x = 1–8 wherein R1 is a substituent of an aromatic ring selected from the group consisting of H, CH$_3$, C$_2$H$_5$, CH$_3$CH$_2$CH$_2$, (CH$_3$)$_2$CH, (CH$_3$)$_3$C, a halogen atom, CN, NO$_2$, COOR', and SO$_2$R", wherein R' is selected from the group consisting of H, Na, K, CH$_3$, and C$_2$H$_5$, and R" is selected from the group consisting of OH, a halogen atom, ONa, OK, OCH$_3$, and OC$_2$H$_5$; and x represents an integer of 1 to 8 being the same or different each other in the polyhydroxyalkanoate, comprising the step of:
cultivating a microorganism in a culture medium containing a compound represented by the following chemical formula (10):

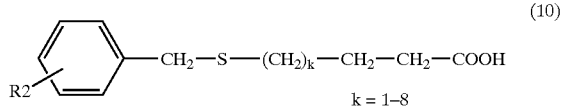

k = 1–8 wherein R2 is a substituent of an aromatic ring and selected the group consisting of H, CH$_3$, C$_2$H$_5$, CH$_3$CH$_2$CH$_2$, (CH$_3$)$_2$CH, (CH$_3$)$_3$C, a halogen atom, CN, NO$_2$, COOR' and SO$_2$R", wherein R' is selected from the group consisting of H, Na, K, CH$_3$, and C$_2$H$_5$, and R" is selected from the group consisting of OH, a halogen atom, ONa, OK, OCH$_3$, and OC$_2$H$_5$; and k represents an integer of 1 to 8, wherein the culture medium further contains a straight chain alkanoic acid having 4 to 12 carbon atoms, or a salt thereof.

20. The process according to claim 9, wherein cultivation of the microorganism comprises two or more cultivation steps.

21. The process according to claim 20, wherein the culture medium in the steps later than the first step contains no nitrogen source.

22. The process according to claim 20, wherein the cultivation step comprises the steps of:

(1-1) cultivating the microorganism in a culture medium that contains at least one compound represented by the chemical formula (10) and polypeptone;

(1-2) further cultivating the microorganism from the step 1-1 in a culture medium containing the compound represented by the chemical formula (10) and an organic acid or a salt thereof.

23. The process according to claim 22, wherein the organic acid or a salt thereof is one or more compounds selected from the group consisting of pyruvic acid, malic acid, lactic acid, citric acid, succinic acid and salts thereof.

24. The process according to claim 20, wherein the cultivation step comprises the steps of:

(1-3) cultivating the microorganism in a culture medium containing at least one compound represented by the chemical formula (10) and a saccharide, and (1-4) cultivating the microorganism from the step 1-3 in a culture medium containing the compound represented by the chemical formula (10) and a saccharide.

25. The process according to claim 24, wherein the saccharide is one or more compounds selected from the group consisting of glyceraldehyde, erythrose, arabinose, xylose, glucose, galactose, mannose, fructose, glycerol, erythritol, xylitol, gluconic acid, glucuronic acid, galacturonic acid, maltose, sucrose, and lactose.

26. The process according to claim 9, wherein the microorganism is cultivated in a culture medium containing 5-[(phenylmethyl)sulfanyl]valeric acid represented by the following chemical formula (11) to produce a polyhydroxyalkanoate comprising a unit of 3-hydroxy-5-[(phenylmethyl)sulfanyl]valerate represented by the following chemical formula (2):

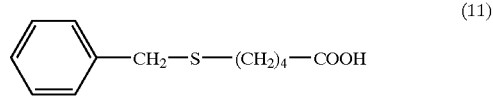

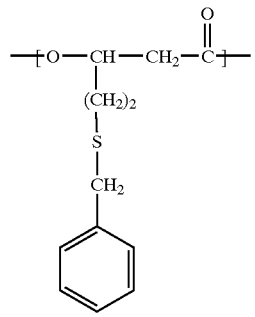

27. The process according to any one of claims 9 to 17, wherein the microorganism is cultivated in a culture medium containing 4-[(phenylmethyl)sulfanyl]butyric acid represented by the following chemical formula (12) to produce a polyhydroxyalkanoate comprising a unit of 3-hydroxy-4-[(phenylmethyl)sulfanyl]butyrate represented by the following chemical formula (6):

(12)
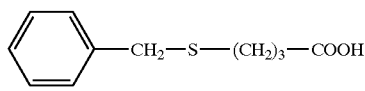

(6)
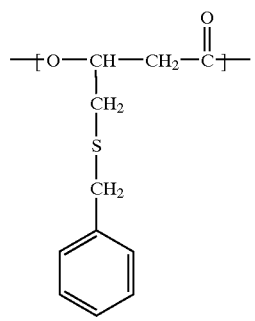

28. The process according to claim 9, wherein the microorganism is cultivated in a culture medium containing 5-{[(4-methylphenyl)methyl]sulfanyl}valeric acid represented by the following chemical formula (13) to produce a polyhydroxyalkanoate comprising a unit of 3-hydroxy-5-{[(4-methylphenyl)methyl]sulfanyl}valerate represented by the following chemical formula (7):

(13)

(7)
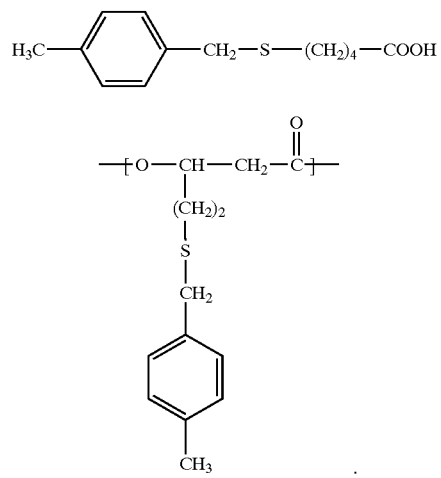

29. The process according to claim 9, wherein the microorganism is cultivated in a culture medium that contains 5-{[(4-fluorophenyl)methyl]sulfanyl}valeric acid represented by the following chemical formula (14):

(14)
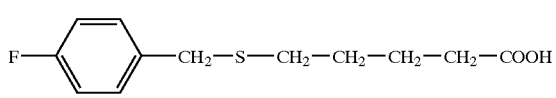

to produce a polyhydroxyalkanoate comprising a unit of 3-hydroxy-5-{[(4-fluorophenyl)methyl]sulfanyl}valerate represented by the following chemical formula (8):

(8)
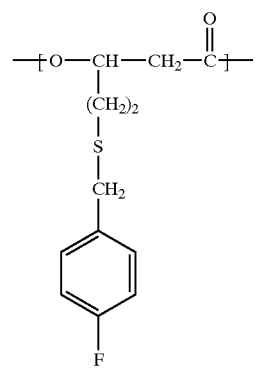

30. The process according to claim 9, wherein the microorganism is cultivated in a culture medium containing 4-{[(4-fluorophenyl)methyl]sulfanyl}butyric acid represented by the following chemical formula (15):

(15)
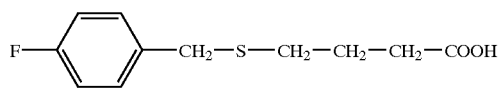

to produce a polyhydroxyalkanoate comprising a unit of 3-hydroxy-4-{[(4-fluorophenyl)methyl]sulfanyl}butyrate represented by the following chemical formula (9):

(9)
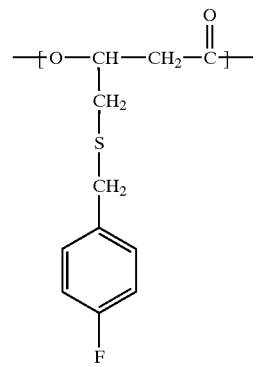

31. The process according to claim 9, further comprising the step of isolating the polyhydroxyalkanoate from cells of the microorganism cultivated in the cultivation step.

32. The process according to claim 31, wherein the step of isolating the polyhydroxyalkanoate comprises the step of treating with a solvent to solubilize and extract the polyhydroxyalkanoate accumulated in the cells of the microorganism cultivated in the cultivation step.

33. The process according to claim 32, wherein the solvent is one or more solvents selected from the group consisting of chloroform, dichloromethane, dioxane, tetrahydrofuran, acetonitrile, and acetone.

34. The process according to claim 31, wherein the step of isolating the polyhydroxyalkanoate comprises the step of disrupting cells of the microorganism.

35. The process according to claim 34, wherein the cells are disrupted by ultrasonic disruption, homogenization, pressure disruption, disruption with glass beads, trituration, grinding or freeze-thawing.-

36. The process according to claim 9, wherein the microorganism belongs to genus *Pseudomonas*.

37. The process according to claim 36, wherein the microorganism that belongs to genus *Pseudomonas* is selected from the group consisting of *Pseudomonas cichorii* YN2 (FERM BP-7375), *Pseudomonas cichorii* H45 (FERM PB-7374), and *Pseudomonas jessenii* P161 (FERM BP-7376).

* * * * *

UNITED STATES PATENT AND TRADEMARK OFFICE
CERTIFICATE OF CORRECTION

PATENT NO. : 6,911,521 B2
DATED : June 28, 2005
INVENTOR(S) : Takashi Kenmoku et al.

It is certified that error appears in the above-identified patent and that said Letters Patent is hereby corrected as shown below:

Title page,
Item [30], Foreign Application Priority Data,
"2001/165239" should read -- 2001-165239 --;
"2001/165357" should read -- 2001-165357 --;
"2001/209898" should read -- 2001-290898 --;
"2001/210039" should read -- 2001-210039 --; and
"2001/039259" should read -- 2001-039259 --.
Item [56], References Cited, OTHER PUBLICATIONS,
"Young B. Kim t al.," should read -- Young B. Kim et al., --; and
"Katsutoshi Hori et al.," reference, "Fluoroalk" should read -- Fluoroalk- --.

Column 3,
Line 38, "3-hydroxy-ω-[{" should read -- 3-hydroxy-ω-{ --.

Column 5,
Line 48, "accumulated" should read -- accumulation --.

Column 6,
Line 10, "was" should read -- were --; and
Line 11, "is" should read -- are --.

Column 13,
Line 39, "200 lb mL" should read -- 200 mL --.

Column 19,
Line 65, "3-hydroxyalkanoicates" should read -- 3-hydroxyalkanoates --.

Column 22,
Line 61, "methyl)" should read -- methyl] --.

Column 23,
Line 65, "sulfanyl)" should read -- sulfanyl} --.

Column 26,
Line 66, "yield." should read -- yield --.

Column 27,
Line 11, "$^3$H-NMR" should read -- $^1$H-NMR --; and
Line 22, "5-([(4-" should read -- 5-{[(4- --.

UNITED STATES PATENT AND TRADEMARK OFFICE
CERTIFICATE OF CORRECTION

PATENT NO. : 6,911,521 B2
DATED : June 28, 2005
INVENTOR(S) : Takashi Kenmoku et al.

It is certified that error appears in the above-identified patent and that said Letters Patent is hereby corrected as shown below:

Column 31,
Line 7, "PRA" should read -- PHA --.

Column 32,
Line 67, "4-{[[4-fluoromethyl]phenyl]" should read -- 4-{[[(4-fluoromethyl)phenyl]" --.

Column 33,
Line 1, "methyl}sulfanyl]butyric" should read -- methyl]sulfanyl}butyric --.

Column 35,
Line 30, "different" should read -- different from --.

Column 36,
Line 64, "claim 1, the" should read -- claim 1, wherein the --.

Column 38,
Line 28, "different" should read -- different from --;
Line 44, "selected" should read -- selected from --;
Line 48, "wherein R''" should read -- wherein R' --; and
Line 51, "$OC_2Hs$;" should read -- $OC_2H_5$; --.

Column 39,
Line 44, "different" should read -- different from --; and
Line 56, "selected" should read -- selected from --.

Column 40,
Line 24, "different" should read -- different from --; and
Line 36, "selected" should read -- selected from --.

Column 41,
Lines 5 and 62, "different" should read -- different from --; and
Line 18, "selected" should read -- selected from --.

Column 42,
Line 8, "selected" should read -- selected from --; and
Line 53, "different" should read -- different from --.

UNITED STATES PATENT AND TRADEMARK OFFICE
CERTIFICATE OF CORRECTION

PATENT NO. : 6,911,521 B2
DATED : June 28, 2005
INVENTOR(S) : Takashi Kenmoku et al.

It is certified that error appears in the above-identified patent and that said Letters Patent is hereby corrected as shown below:

Column 43,
Lines 1 and 53, "selected" should read -- selected from --; and
Line 41, "different" should read -- different from --.

Column 44,
Line 6, "polypeptone;" should read -- polypeptone; and --; and
Line 21, "saccharide, and" should read -- saccharide; and --.

Column 46,
Line 67, "freeze-thawing.-" should read -- freeze-thawing. --.

Signed and Sealed this

Twenty-ninth Day of November, 2005

JON W. DUDAS
*Director of the United States Patent and Trademark Office*